(12) United States Patent
Tsukamoto et al.

(10) Patent No.: US 9,273,050 B2
(45) Date of Patent: Mar. 1, 2016

(54) CYCLOBUTYL PURINE DERIVATIVE, ANGIOGENESIS PROMOTING AGENT, LUMEN FORMATION PROMOTING AGENT, NEUROCYTE GROWTH PROMOTING AGENT, AND DRUG

(75) Inventors: Ikuko Tsukamoto, Kita-gun (JP); Ryoji Konishi, Kita-gun (JP); Masaaki Tokuda, Kita-gun (JP); Yasuo Kubota, Kita-gun (JP); Tokumi Maruyama, Sanuki (JP); Hiroaki Kosaka, Kita-gun (JP); Junsuke Igarashi, Kita-gun (JP)

(73) Assignee: National University Corporation Kagawa University, Kagawa (JP)

( * ) Notice: Subject to any disclaimer, the term of this patent is extended or adjusted under 35 U.S.C. 154(b) by 351 days.

(21) Appl. No.: 13/130,952

(22) PCT Filed: Nov. 27, 2009

(86) PCT No.: PCT/JP2009/070062
§ 371 (c)(1),
(2), (4) Date: May 24, 2011

(87) PCT Pub. No.: WO2010/061931
PCT Pub. Date: Jun. 3, 2010

(65) Prior Publication Data
US 2011/0230659 A1 Sep. 22, 2011

(30) Foreign Application Priority Data
Nov. 27, 2008 (JP) ................. 2008-303239

(51) Int. Cl.
*C07D 473/34* (2006.01)
*C07D 473/40* (2006.01)
*C07D 473/18* (2006.01)
*C07D 473/24* (2006.01)

(52) U.S. Cl.
CPC ............ *C07D 473/18* (2013.01); *C07D 473/24* (2013.01); *C07D 473/34* (2013.01); *C07D 473/40* (2013.01)

(58) Field of Classification Search
USPC ....................................... 544/276
See application file for complete search history.

(56) References Cited

U.S. PATENT DOCUMENTS

| | | | |
|---|---|---|---|
| 5,126,345 A | 6/1992 | Slusarchyk et al. | |
| 5,130,462 A | 7/1992 | Slusarchyk et al. | |
| 5,153,352 A | 10/1992 | Norbeck et al. | |
| 5,185,459 A | 2/1993 | Slusarchyk et al. | |
| 5,283,331 A | 2/1994 | Saito et al. | |
| 5,324,730 A | 6/1994 | Ichikawa et al. | |
| 5,723,609 A | 3/1998 | Slusarchyk et al. | |
| 6,288,113 B1 | 9/2001 | Egi et al. | |
| 6,384,063 B1 | 5/2002 | Saito et al. | |
| 2003/0045533 A1 | 3/2003 | Liu et al. | |
| 2004/0157864 A1 | 8/2004 | Wu et al. | |
| 2004/0242598 A1 | 12/2004 | Liu et al. | |
| 2004/0266696 A1 | 12/2004 | Nokihara et al. | |
| 2008/0119495 A1 | 5/2008 | Liu et al. | |
| 2010/0010020 A1 | 1/2010 | Liu et al. | |

FOREIGN PATENT DOCUMENTS

| | | |
|---|---|---|
| CN | 1036575 | 10/1989 |
| CN | 1501927 | 6/2004 |
| EP | 0 335 355 | 10/1989 |
| EP | 0358154 A2 | 3/1990 |
| JP | 2-006478 | 1/1990 |

(Continued)

OTHER PUBLICATIONS

Mayo Clinic. Alzheimer's disease: Prevention. Jan. 19, 2013. < http://www.mayoclinic.com/health/alzheimers-disease/DS00161/DSECTION=prevention>.*
Mayo Clinic. Heart attack: Prevention. May 15, 2013. < http://www.mayoclinic.com/health/heart-attack/DS00094/DSECTION=prevention>.*
English, Jessie M. TRENDS in Pharmacological Sciences vol. 23 No. 1 Jan. 2002.*
IUPAC Compendium of Chemical Terminology, Version 2.3.2. Aug. 19, 2012, 1535-1538.*
Wermuth, Camille G."Molecular Variations Based on Isoteric Replacements." The Practice of Medicinal Chemistry. Academic Press, 1996. pp. 203-237.*
Morissette, Sherry. Adv. Drug Delivery Rev. 2004, 56, 275-300.*
Rouhi, Maureen. Chem. & Eng. News, 2003, 81(8), 32-35.*

(Continued)

*Primary Examiner* — Golam M M Shameem
*Assistant Examiner* — Laura Daniel
(74) *Attorney, Agent, or Firm* — Hamre, Schumann, Mueller & Larson, P.C.

(57) ABSTRACT

Provided is a compound having at least one selected from the group consisting of cell growth promoting activity, angiogenesis promoting activity, lumen formation promoting activity, cell migration promoting activity, and neurocyte growth promoting activity, which is a chemically stable low-molecular-weight substance that has high absorbability and can be supplied stably at a low cost because of its low molecular weight. A cyclobutyl purine derivative, a tautomer or stereoisomer thereof, or a salt, solvate, or hydrate thereof according to the present invention is a cyclobutyl purine derivative represented by the following general formula (1), a tautomer or stereoisomer thereof, or a salt, solvate, or hydrate thereof.

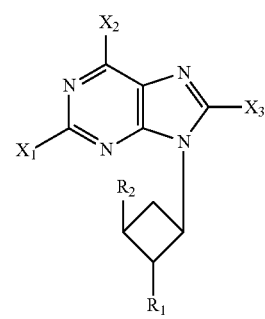

(1)

5 Claims, 9 Drawing Sheets

(56) References Cited

FOREIGN PATENT DOCUMENTS

| | | |
|---|---|---|
| JP | 3-47169 | 2/1991 |
| JP | 5-32691 | 2/1993 |
| JP | 8-301765 | 11/1996 |
| JP | 2577640 B2 | 11/1996 |
| JP | 2694999 B2 | 9/1997 |
| JP | 2962494 B2 | 8/1999 |
| JP | 11-263770 | 9/1999 |
| JP | 2004-528391 | 9/2004 |
| JP | 2006-513253 | 4/2006 |
| JP | 2007-531729 | 11/2007 |
| WO | WO 99/09992 A1 | 3/1999 |
| WO | 02/098878 | 12/2002 |
| WO | WO 03/030925 A1 | 4/2003 |
| WO | 2004/035132 | 4/2004 |
| WO | 2005/097140 | 10/2005 |

OTHER PUBLICATIONS

Byrn, Stephen. Solid-State Chemistry of Drugs, 2d, Chapter 11 Hydrates and Solvates/hydrates (1999) 233-247, 233.*

Thornber, C.W. Chem. Soc. Rev. 8. (1979), 563-580.*

Schultheiss, Caroline. Angiogenesis (2006) 9:59-65.*

MedicineNet. Infarction Definition. (2015). pp. 1-3. < http://www.medicinenet.com/script/main/art.asp?articlekey=3970>.*

Dorland's Medical Dictionary. nfarction. (n.d.) Dorland's Medical Dictionary for Health Consumers. (2007). pp. 1-4. Retrieved May 13, 2015 from http://medical-dictionary.thefreedictionary.com/infarction.*

Yano, Kiichiro. J. Clin Invest. 107:4 (2001) 409-417.*

Tonnesen, Marcia. JID Symposium Proceedings. 5:40 (2000) 40-46.*

Mayo Clinic. Hair Loss. Diseases and Conditions. (2015). pp. 1-8. <http://www.mayoclinic.org/diseases-conditions/hair-loss/basics/causes/con-20027666>.*

Medline Plus. Wounds and Injuries. NIH. (2015) pp. 1-10. <http://www.nlm.nih.gov/medlineplus/woundsandinjuries.html>.*

Nandanan, et al., "Synthesis Biological Activity, and Molecular Modeling of Ribose-Modified Deoxyadenosine Bisphosphate Analogues as $P2Y_1$ Receptor Ligands", J. Med. Chem., vol. 43, pp. 829-842 (2000).

Tsukamoto et al., "Synthesis of a nucleic acid analogue 2C1-C. OXT-A and its angiogenic activity," Abstract of Medicinal Chemistry Symposium, 28, pp. 72-73, 2009.

Tsukamoto et al., "Action of Nucleic Acid Analogue 2C1-C. OXT-A to Promote Lumen Formation by HUVEC," The 17th Annual Meeting of the Japanese Vascular Biology and Medicine Organization, p. 63, p. 1-13, 2009.

Jacobson et al., "Structurally related nucleotides as selective agonists and antagonists at P2Y1 receptors," Il Farmaco, vol. 56, pp. 71-75, 2001.

Honzawa et al., "Synthesis and Hybridization Property of Oligonucleotides Containing Carbocyclic Oxetanocins," Tetrahedron, vol. 56, pp. 2615-2627, 2000.

Bisacchi et al., "Synthesis and Antiviral Activity of Enantiomeric Forms of Cyclobutyl Nucleoside Analogues," Journal of Medicinal Chemistry, vol. 34, No. 4, pp. 1415-1421, 1991.

Ellman et al., "A New and Rapid Colorimetric Determination of Acetylcholinesterase Activity," Biochemical Pharmacology, vol. 7, pp. 88-95, 1961.

Tsukamoto et al., "A novel nucleic acid analogue shows strong angiogenic activity," Biochemical and Biophysical Research Communications, vol. 399, pp. 699-704, 2010.

"Khimicheskii enciklopedicheskii slovar", Moskva, "Sovetskaya enciklopedia", 1983, p. 533.

N.A. Tyukavkina I dr., Bioorganicheskaya khimiya, 4-oe izdanie, "Drofa", Moskva, 2005, pp. 83-85.

M.D. Mashkovsky "Lekarstvennie sredstva", Moskva, "Novaya volna", 2001, vol. 1, p. 14.

* cited by examiner

Photographs of formed lumen (CD31 staining)    Horizontal width 6 mm

Comp. Ex. 8

Comp. Ex. 7

Ex. 1 (1 μmol/L)

Ex. 1 (10 μmol/L)

Ex. 1 (100 μmol/L)

Ex. 1 (1 mmol/L)

Control

Comp. Ex. 8

Comp. Ex. 9

Comp. Ex. 10

Comp. Ex. 7

Ex. 1 (10 μmol/L)

Ex. 1 (50 μmol/L)

Ex. 1 (100 μmol/L)

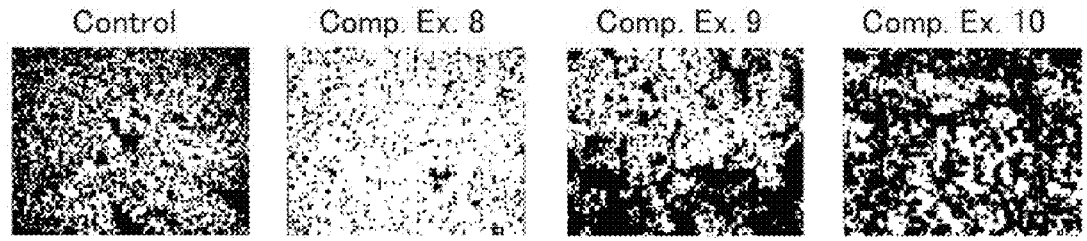
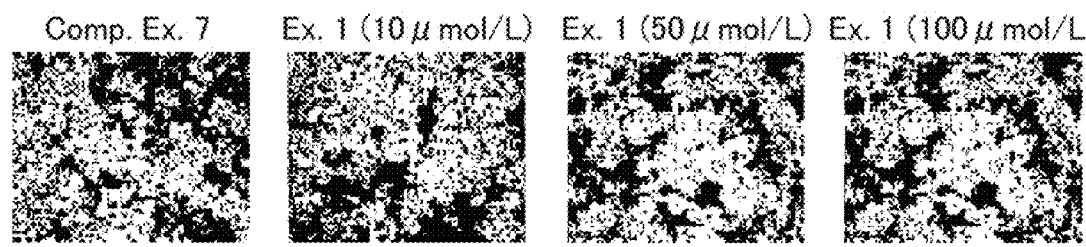
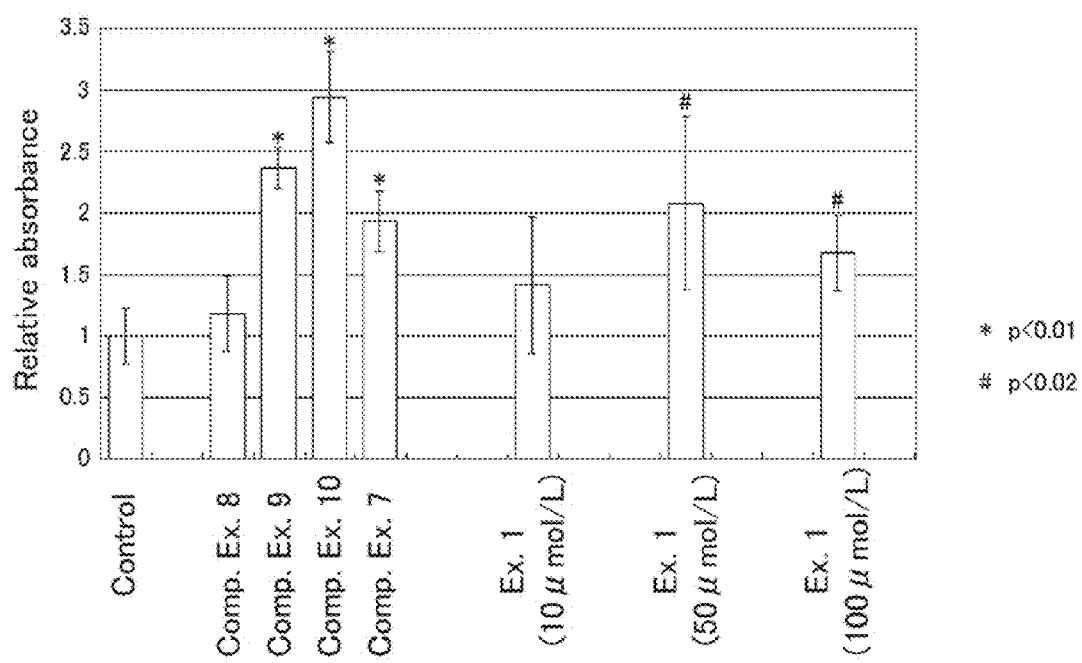
FIG. 6

CYCLOBUTYL PURINE DERIVATIVE, ANGIOGENESIS PROMOTING AGENT, LUMEN FORMATION PROMOTING AGENT, NEUROCYTE GROWTH PROMOTING AGENT, AND DRUG

TECHNICAL FIELD

The present invention relates to a cyclobutyl purine derivative, an angiogenesis promoting agent, a lumen formation promoting agent, a neurocyte growth promoting agent, and a drug.

BACKGROUND ART

It is conventionally known that some derivatives having a nucleic acid bound to then four-membered rings have antiviral action. Examples of such derivatives include cyclobutyl purine derivatives (see Patent Documents 1 to 3, for example) and oxetanocin derivatives having a nucleic acid bound to their oxetane rings (see Patent Document 4, for example).

On the other hand, as substances that promote angiogenesis, neurocyte growth, and the like, living organism-derived growth factors such as fibroblast growth factors (FGFs), platelet-derived growth factors (PD-ECGFs), vascular endothelial growth factors (VEGFs), and nerve growth factors (NGFs) are known. Some of these growth factors are used as active ingredients in wound healing agents, hair growth agents, and the like.

CITATION LIST

Patent Documents

Patent Document 1: Japanese Patent No. 2694999
Patent Document 2: Japanese Patent No. 2577640
Patent Document 3: Japanese Patent No. 2962494
Patent Document 4: JP 5 (1993)-32691 A

BRIEF SUMMARY OF THE INVENTION

Problem to be Solved by the Invention

However, the above-described growth factors are all high molecular proteins having a molecular weight from 15000 to 30000. Thus, they have a problem of low absorbability and low stability. With this in mind, it is an object of the present invention to provide a compound having at least one of angiogenesis promoting-activity, lumen formation promoting-activity, and neurocyte growth promoting-activity, which is a chemically stable low molecular weight substance that has high absorbability and can be supplied stably at a low cost because of its low molecular weight.

Means for Solving Problem

The present invention provides a cyclobutyl purine derivative represented by the following general formula (1), a tautomer or stereoisomer thereof, or a salt, solvate, or hydrate thereof.

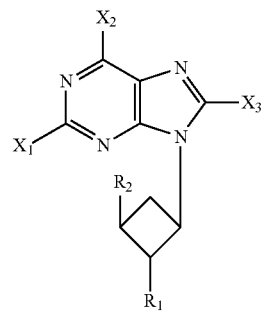

In the general formula (1),
X$_1$ is a halogeno group, an alkyl group, an alkylthio group, a thio group (thiol group), an amino group, a hydroxy group, an alkoxy group, an alkynyl group, or a cyano group;
X$_2$ is a halogeno group, an amino group, a hydroxy group, an alkoxy group, a thio group (thiol group), or an alkylthio group;
X$_3$ is a hydrogen atom, a halogeno group, or an alkoxy group;
R$_1$ and R$_2$ are the same or different, and are each independently a hydrogen atom, a halogeno group, a carboxyl group, an alkyl group, an acyl group, a carbamoyl group, an acyloxy group, a hydroxyalkyl group, an acyloxyalkyl group, an alkoxyalkyl group, a haloalkyl group, or a phosphonooxyalkyl group;
when X$_1$ is an amino group,
X$_2$ and X$_3$ are both halogeno groups,
X$_2$ and X$_3$ are both alkoxy groups, or
X$_2$ is a hydroxy group, X$_3$ is a halogeno group, and R$_1$ and R$_2$ are both acyloxyalkyl groups; and
in X$_1$, X$_2$, X$_3$, R$_1$, and R$_2$, at least one hydrogen atom in each of the alkyl group, the alkylthio group, the thio group (thiol group), the hydroxy group, the alkoxy group, the alkynyl group, the amino group, the carboxyl group, the acyl group, the carbamoyl group, the acyloxy group, the hydroxyalkyl group, the acyloxyalkyl group, the alkoxyalkyl group, and the phosphonooxyalkyl group may be substituted with an arbitrary substituent.

Effects of the Invention

In order to achieve the above object, the inventors of the present invention have conducted a series of studies. As a result, they discovered a novel cyclobutyl purine derivative represented by the general formula (1), having at least one of angiogenesis promoting-activity, lumen formation promoting-activity, and neurocyte growth promoting-activity, thereby achieving the present invention. The cyclobutyl purine derivative according to the present invention is a chemically stable low molecular weight substance. Because of its low molecular weight, the cyclobutyl purine derivative according to the present invention has high absorbability and can be supplied stably at a low cost. The cyclobutyl purine derivative according to the present invention can be used in various drugs, quasi drugs, and the like that utilize at least one of angiogenesis promoting-activity, lumen formation promoting-activity, and neurocyte growth promoting-activity.

BRIEF DESCRIPTION OF DRAWINGS

FIGS. 5A to 5H are photographs showing the results of the cell migration measurement in Example 1 and Comparative Examples 7 to 10.

FIG. 6 is a graph showing the results of the cell migration measurement in Example 1 and Comparative Examples 7 to 10.

FIG. 15 shows micrographs of PC12 cells in Example 10.

FIG. 17 shows photographs showing the results of an angiogenesis test according to the rabbit cornea assay in Example 11.

MODE FOR CARRYING OUT THE INVENTION

Figure 1:
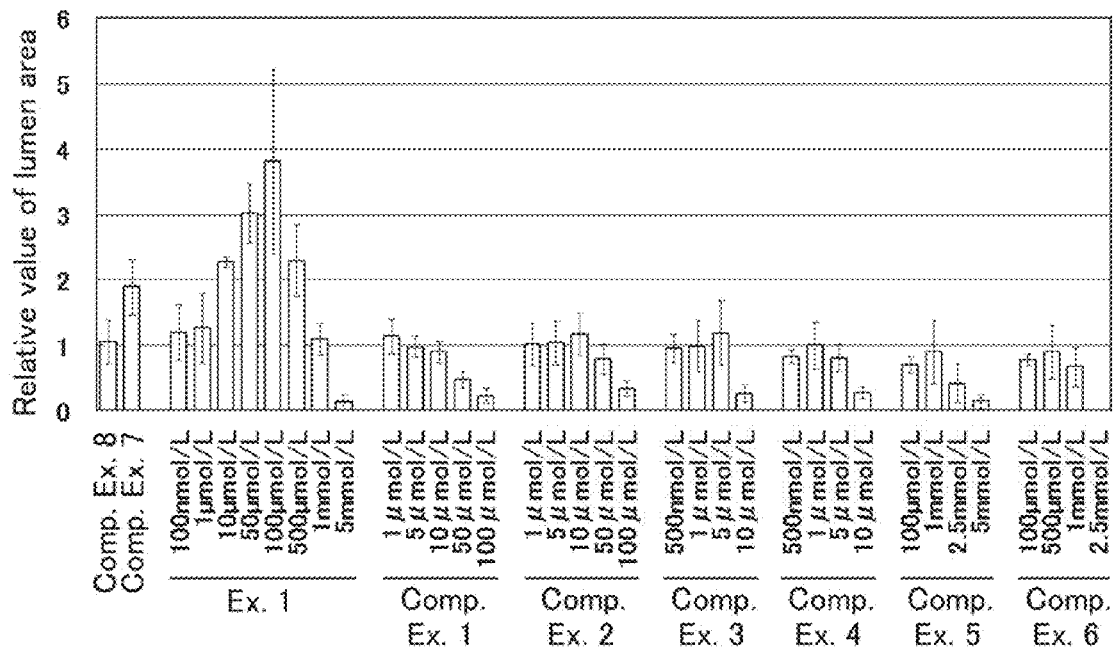
FIG. 1 is a graph showing the results of the lumen formation measurement in Example 1 and Comparative Examples 1 to 8.

The cyclobutyl purine derivative, the tautomer or stereoisomer thereof, or the salt, solvate, or hydrate thereof according to the present invention preferably is such that, in the general formula (1), $X_1$ is a chloro group, for example.

The cyclobutyl purine derivative, the tautomer or stereoisomer thereof, or the salt, solvate, or hydrate thereof according to the present invention preferably is such that, in the general formula (1), $X_2$ is an amino group, for example.

The cyclobutyl purine derivative, the tautomer or stereoisomer thereof, or the salt, solvate, or hydrate thereof according to the present invention preferably is such that, in the general formula (1), $R_1$ and $R_2$ are hydroxymethyl groups, for example.

The cyclobutyl purine derivative, the tautomer or stereoisomer thereof, or the salt, solvate, or hydrate thereof according to the present invention may be such that, in the general formula (1), $X_1$ is a chloro group, $X_2$ is an amino group, and $R_1$ and $R_2$ are hydroxymethyl groups, for example.

The cyclobutyl purine derivative, the tautomer or stereoisomer thereof, or the salt, solvate, or hydrate thereof according to the present invention may be 6-amino-2-chloro-9-[trans-trans-2,3-bis(hydroxymethyl)cyclobutyl]purine or 6-amino-2-thiomethoxy-9-[trans-trans-2,3-bis (hydroxymethyl)cyclobutyl]purine, a tautomer or stereoisomer thereof, or a salt, solvate, or hydrate thereof, for example.

The present invention also provides a promoting agent having at least one function selected from the group consisting of an angiogenesis-promoting function, a lumen formation-promoting function, and a neurocyte growth-promoting function, containing a cyclobutyl purine derivative represented by the following general formula (1'), a tautomer or stereoisomer thereof, or a salt, solvate, or hydrate thereof.

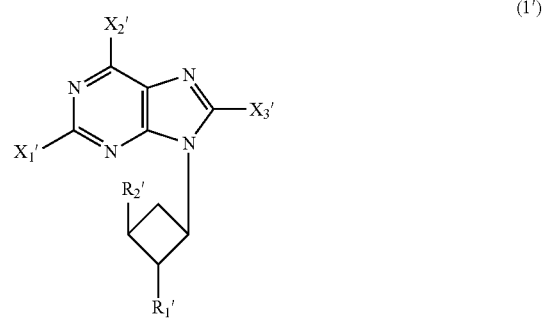

(1')

In the general formula (1'), $X_{1'}$ is a halogeno group, an alkyl group, an alkylthio group, a thio group (thiol group), an amino group, a hydroxy group, an alkoxy group, an alkynyl group, or a cyano group;

$X_{2'}$ is a halogeno group, an amino group, a hydroxy group, an alkoxy group, a thio group (thiol group), or an alkylthio group;

$X_{3'}$ is a hydrogen atom, a halogeno group, an alkyl group, an alkylthio group, an amino group, a hydroxy group, an alkoxy group, a hydroxyphenyl group, or a carbamoyl group;

$R_{1'}$ and $R_{2'}$ are the same or different, and are each independently a hydrogen atom, a halogeno group, a carboxyl group, an alkyl group, an acyl group, a carbamoyl group, an acyloxy group, a hydroxyalkyl group, an acyloxyalkyl group, an alkoxyalkyl group, a haloalkyl group, or a phosphonooxyalkyl group;

when $X_{1'}$ is an amino group and $X_{3'}$ is a hydrogen atom, $R_{1'}$ and $R_{2'}$ are each independently an atom or substituent other than a hydroxyalkyl group; and in $X_{1'}$, $X_{2'}$, $X_{3'}$, $R_{1'}$, and $R_{2'}$, at least one hydrogen atom in each of the alkyl group, the alkylthio group, the thio group (thiol group), the hydroxy group, the alkoxy group, the alkynyl group, the amino group, the hydroxyphenyl group, the carbamoyl group, the carboxyl group, the acyl group, the acyloxy group, the hydroxyalkyl group, the acyloxyalkyl group, the alkoxyalkyl group, and the phosphonooxyalkyl group may be substituted with an arbitrary substituent.

The promoting agent according to the present invention may be such that, in the general formula (1'), $X_{1'}$ is a chloro group, for example.

The promoting agent according to the present invention may be such that, in the general formula (1'), $X_{2'}$ is an amino group, for example.

The promoting agent according to the present invention may be such that, in the general formula (1'), $R_{1'}$ and $R_{2'}$ are hydroxymethyl groups, for example.

The promoting agent according to the present invention may be such that, in the general formula (1'), $X_{1'}$ is a chloro group or a thiomethoxy group, $X_{2'}$ is an amino group, $X_{3'}$ is a hydrogen atom, and $R_{1'}$ and $R_{2'}$ are hydroxymethyl groups, for example.

The promoting agent according to the present invention may contain 6-amino-2-chloro-9-[trans-trans-2,3-bis(hydroxymethyl)cyclobutyl]purine or 6-amino-2-thiomethoxy-9-[trans-trans-2,3-bis(hydroxymethyl)cyclobutyl]purine, a tautomer or stereoisomer thereof, or a salt, solvate, or hydrate thereof, for example.

The present invention also provides a drug for use in at least one selected from the group consisting of promoting angiogenesis, promoting lumen formation, and promoting neurocyte growth, containing at least one selected from the group consisting of the cyclobutyl purine derivative, the tautomers and stereoisomers thereof, the salts, solvates, and hydrates thereof according to the present invention, and the promoting agent according to the present invention.

The drug according to the present invention may be at least one selected from the group consisting of wound healing agents, therapeutic agents for Alzheimer's disease, prophylactic agents for Alzheimer's disease, therapeutic agents for infarction diseases, prophylactic agents for infarction diseases, and hair growth agents, for example.

In the following, the present invention will be described in further detail.

In the present invention, a halogeno group is not particularly limited, and examples thereof include a fluoro group (fluorine atom), a chloro group (chlorine atom), a bromo group (bromine atom), and an iodo group (iodine atom). The term "halogeno group" is a name used to refer to a halogen atom as a substituent.

In the present invention, an alkyl group is not particularly limited, and examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, and a tert-pentyl group. The same applies to groups including an alkyl group in their structures, such as an alkylamino group or an alkoxy group. In the present invention, at least one hydrogen atom in the alkyl group may be substituted with an arbitrary substituent, for example. The substituent in the alkyl group is not particularly limited, and examples thereof include a hydroxy group, a halogeno group, an acyl group, an acyloxy group, an alkoxy group, and a carbamoyl group.

In the present invention, an alkylthio group is not particularly limited, and examples thereof include a methylthio group, an ethylthio group, an n-propylthio group, and an isopropylthio group. In the present invention, at least one hydrogen atom in the alkylthio group may be substituted with an arbitrary substituent, for example. The substituent in the alkylthio group is not particularly limited, and examples thereof include a hydroxy group, a halogeno group, an acyl group, an acyloxy group, and an alkoxy group.

In the present invention, the hydrogen atom in a thio group (thiol group) may be substituted with an arbitrary substituent, for example. The substituent in the thio group (thiol group) is not particularly limited, and examples thereof include a methyl group, a tert-butyl group, a benzyl group, a p-methoxybenzyl group, a methoxymethyl group, an acetyl group, a pivaloyl group, a benzoyl group, a dimethoxytrityl group, a monomethoxytrityl group, and a pixyl group.

In the present invention, a hydroxy group may be present in the form of an oxo group ($=$O) as a result of isomerization, and the hydrogen atom therein may be substituted with an arbitrary substituent, for example. The substituent in the hydroxy group encompasses those that can be deprotected with acid, and is not particularly limited. Examples of the substituent include a methyl group, a tert-butyl group, a benzyl group, a p-methoxybenzyl group, a methoxymethyl group, an acetyl group, a pivaloyl group, a benzoyl group, a dimethoxytrityl group, a monomethoxytrityl group, and a pixyl group.

In the present invention, an alkoxy group is not particularly limited, and examples thereof include a methoxy group, an ethoxy group, a propoxy group, and a butoxy group. In the present invention, at least one hydrogen atom in the alkoxy group may be substituted with an arbitrary substituent, for example. The substituent in the alkoxy group is not particularly limited, and examples thereof include a hydroxy group, a halogeno group, an acyl group, an acyloxy group, an alkoxy group, and a carbamoyl group.

In the present invention, an alkynyl group is not particularly limited, and examples thereof include substituents represented by the following general formula (2) (where R denotes a hydrogen atom or a straight-chain or branched alkyl group). Specific examples of the substituents include an ethynyl group and a propargyl group. In the present invention, at least one hydrogen atom in the alkynyl group may be substituted with an arbitrary substituent, for example. The substituent in the alkynyl group is not particularly limited, and examples thereof include a hydroxy group, a halogeno group, an acyl group, an acyloxy group, and an alkoxy group.

$$R-C\equiv C- \quad (2)$$

In the present invention, at least one hydrogen atom in an amino group may be substituted with an arbitrary substituent, for example. The substituent in the amino group is not particularly limited, and examples thereof include: alkyl groups such as a methyl group and an ethyl group; alkylcarbonyl groups having 1 to 6 carbon atoms, such as an acetyl group and ethylcarbonyl; alkylsulfonyl groups having 1 to 6 carbon atoms; alkoxycarbonyl groups having 1 to 6 carbon atoms, such as a methoxycarbonyl group and an ethoxycarbonyl group; arylcarbonyl groups such as a phenylcarbonyl group and a naphthylcarbonyl group; arylsulfonyl groups such as phenylsulfonyl group and a naphthylsulfonyl group; aralkylcarbonyl groups having 7 to 10 carbon atoms, such as a benzylcarbonyl group; aralkyl groups such as a benzyl group, a diphenylmethyl group, and a trityl group; an oxycarbonyl group; a tert-butyloxycarbonyl group; a benzyloxycarbonyl group; an allyloxycarbonyl group; a fluorenylmethyloxycarbonyl group; a trifluoroacetyl group; and a formyl group. These substituents may be substituted with 1 to 3 halogeno groups, nitro groups, or the like. Specific examples of the group resulting from such substitution include a p-nitrobenzyloxycarbonyl group, a p-chlorobenzyloxycarbonyl group, an m-chlorobenzyloxycarbonyl group, and a p-methoxybenzyloxycarbonyl group.

In the present invention, the hydrogen atom in a carboxyl group may be substituted with an arbitrary substituent, for example. The substituent in the carboxyl group is not particularly limited, and examples thereof include a methyl group, a tert-butyl group, a benzyl group, a p-methoxybenzyl group, a methoxymethyl group, an acetyl group, a pivaloyl group, a benzoyl group, a dimethoxytrityl group, a monomethoxytrityl group, and a pixyl group.

In the present invention, an acyl group is not particularly limited, and examples thereof include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group. The same applies to groups including an acyl group in their structures (such as an acyloxy group and an alkanoyloxy group). In the present invention, the number of carbon atoms in the acyl group encompasses the number of carbonyl carbon atoms. For example, an acyl group having one carbon atom denotes a formyl group. In the present invention, at least one hydrogen atom in the acyl group may be substituted with an arbitrary substituent, for example. The substituent in the acyl group is not particularly limited, and examples thereof include a hydroxy group, a halogeno group, an acyl group, an acyloxy group, an alkoxy group, and a carbamoyl group.

In the present invention, at least one hydrogen atom in a carbamoyl group may be substituted with an arbitrary substituent, for example. The substituent in the carbamoyl group is not particularly limited, and examples thereof include: alkyl groups such as a methyl group and an ethyl group; alkylcarbonyl groups having 1 to 6 carbon atoms, such as an acetyl group and ethylcarbonyl; alkylsulfonyl groups having 1 to 6 carbon atoms; alkoxycarbonyl groups having 1 to 6 carbon atoms, such as a methoxycarbonyl group and an ethoxycarbonyl group; arylcarbonyl groups such as a phenylcarbonyl group and a naphthylcarbonyl group; arylsulfonyl groups such as phenylsulfonyl group and a naphthylsulfonyl group; aralkylcarbonyl groups having 7 to 10 carbon atoms, such as a benzylcarbonyl group; aralkyl groups such as a benzyl group, a diphenylmethyl group, and a trityl group; an oxycarbonyl group; a tert-butyloxycarbonyl group; a benzyloxycarbonyl group; an allyloxycarbonyl group; a fluorenylmethyloxycarbonyl group; a trifluoroacetyl group; and a formyl group. These substituents may be substituted with 1 to 3 halogeno groups, nitro groups, or the like. Specific examples of the group resulting from such substitution include a p-nitrobenzyloxycarbonyl group, a p-chlorobenzyloxycarbonyl group, an m-chlorobenzyloxycarbonyl group, and a p-methoxybenzyloxycarbonyl group.

In the present invention, an acyloxy group is not particularly limited, and examples thereof include an acetoxy group, a propionyloxy group, a butanoyloxy group, and a 3-chlorobutyryloxy group. In the present invention, at least one hydrogen atom in the acyloxy group may be substituted with an arbitrary substituent, for example. The substituent in the acyloxy group is not particularly limited, and examples thereof include a hydroxy group, a halogeno group, an acyl group, an acyloxy group, an alkoxy group, and a carbamoyl group.

In the present invention, a hydroxyalkyl group is not particularly limited, and examples thereof include a hydroxymethyl group, a hydroxyethyl group, and a hydroxypropyl group. In the present invention, at least one hydrogen atom in the hydroxyalkyl group may be substituted with an arbitrary substituent, for example. The substituent in the hydroxyalkyl group is not particularly limited, and examples thereof include a hydroxy group, a halogeno group, an acyl group, an acyloxy group, an alkoxy group, and a carbamoyl group.

In the present invention, an acyloxyalkyl group is not particularly limited, and examples thereof include the above-described alkyl groups substituted with the above-described acyloxy groups. Examples of the acyloxyalkyl group include an acetoxyethyl group, a propionyloxyethyl group, a butanoyloxyethyl group, and a 3-chlorobutyryloxyethyl group. In the present invention, at least one hydrogen atom in the acyloxyalkyl group may be substituted with an arbitrary substituent, for example. The substituent in the acyloxyalkyl group is not particularly limited, and examples thereof include a hydroxy group, a halogeno group, an acyl group, an acyloxy group, an alkoxy group, and a carbamoyl group.

In the present invention, an alkoxyalkyl group is not particularly limited, and examples thereof include a methoxymethyl group, an ethoxymethyl group, a methoxyethyl group, an ethoxyethyl group, and a propoxyethyl group. In the present invention, at least one hydrogen atom in the alkoxyalkyl group may be substituted with an arbitrary substituent, for example. The substituent in the alkoxyalkyl group is not particularly limited, and examples thereof include a hydroxy group, a halogeno group, an acyl group, an acyloxy group, an alkoxy group, and a carbamoyl group.

In the present invention, a haloalkyl group is not particularly limited, and examples thereof include the above-described alkyl groups substituted with the above-described halogeno groups. Specific examples of the haloalkyl group include a chloromethyl group, a chloroethyl group, a chlorobutyl group, a dichloromethyl group, a trifluoromethyl group, a bromomethyl group, a bromoethyl group, a fluoromethyl group, and a trifluoroethyl group.

In the present invention, a phosphonooxyalkyl group is not particularly limited, and examples thereof include a phosphonooxymethy group, a phosphonooxyethyl group, and a phosphonooxypropyl group. In the present invention, at least one hydrogen atom in the phosphonooxyalkyl group may be substituted with an arbitrary substituent, for example. The substituent in the phosphonooxyalkyl group is not particularly limited, and examples thereof include a hydroxy group, a halogeno group, an acyl group, an acyloxy group, an alkoxy group, and a carbamoyl group.

In the present invention, a hydroxy group in a hydroxyphenyl group may be present in the form of an oxo group ($=$O) as a result of isomerization, and the hydrogen atom therein may be substituted with an arbitrary substituent, for example. The substituent in the hydroxyphenyl group encompasses those that can be deprotected with acid, and is not particularly limited. Examples of the substituent include a methyl group, a tert-butyl group, a benzyl group, a p-methoxybenzyl group, a methoxymethyl group, an acetyl group, a pivaloyl group, a benzoyl group, a dimethoxytrityl group, a monomethoxytrityl group, and a pixyl group.

<Cyclobutyl Purine Derivative>

In the present invention, $X_1$ in the general formula (1) is a halogeno group, an alkyl group, an alkylthio group, a thio group (thiol group), an amino group, a hydroxy group, an alkoxy group, an alkynyl group, or a cyano group. Preferably, $X_1$ is a halogeno group.

When $X_1$ is a halogeno group, the halogeno group is not particularly limited, and examples thereof include a fluoro group (fluorine atom), a chloro group (chlorine atom), a bromo group (bromine atom), and an iodo group (iodine atom). Among them, the chloro group (chlorine atom) is preferable.

When $X_1$ is an alkyl group, the alkyl group is not particularly limited, and examples thereof include straight-chain or branched alkyl groups having 1 to 8 carbon atoms. Specific examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, and a tert-pentyl group. Among them, the methyl group is preferable. At least one hydrogen atom in the alkyl group may be substituted with an arbitrary substituent, for example. The substituent in the alkyl group is not particularly limited, and examples thereof include those described above as examples of the substituent in the alkyl group.

Furthermore, when $X_1$ is an alkylthio group, the alkylthio group is not particularly limited, and examples thereof include straight-chain or branched alkylthio groups having 1 to 8 carbon atoms. Specific examples of the alkylthio group include a methylthio group, an ethylthio group, an n-propylthio group, and an isopropylthio group. Among them, the methylthio group is preferable. At least one hydrogen atom in the alkylthio group may be substituted with an arbitrary substituent, for example. The substituent in the alkylthio group is not particularly limited, and examples thereof include those described above as examples of the substituent in the alkylthio group.

When $X_1$ is a thio group (thiol group), a hydrogen atom in the thio group (thiol group) may be substituted with an arbitrary substituent, for example. The substituent in the thio group (thiol group) is not particularly limited, and examples thereof include those described above as examples of the substituent in the thio group (thiol group).

When $X_1$ is an amino group, at least one hydrogen atom in the amino group may be substituted with a different substituent, for example. The substituent in the amino group is not particularly limited, and examples thereof include those described above as examples of the substituent in the amino group.

When $X_1$ is an amino group, $X_2$ and $X_3$ are both halogeno groups; $X_2$ and $X_3$ are both alkoxy groups; or $X_2$ is a hydroxy group, $X_3$ is a halogeno group, and $R_1$ and $R_2$ are both acyloxyalkyl groups.

When $X_1$ is a hydroxy group, the hydroxy group may be present in the form of an oxo group (=O) as a result of isomerization, and the hydrogen atom therein may be substituted with an arbitrary substituent, for example. The substituent in the hydroxy group is not particularly limited, and examples thereof include those described above as examples of the substituent in the hydroxy group.

When $X_1$ is an alkoxy group, the alkoxy group is not particularly limited, and examples thereof include straight-chain or branched alkoxy groups having 1 to 8 carbon atoms. Specific examples of the alkoxy group include a methoxy group, an ethoxy group, a propoxy group, and a butoxy group. At least one hydrogen atom in the alkoxy group may be substituted with an arbitrary substituent, for example. The substituent in the alkoxy group is not particularly limited, and examples thereof include those described above as examples of the substituent in the alkoxy group. When $X_1$ is an alkynyl group, the alkynyl group is not particularly limited, and examples thereof include straight-chain or branched alkynyl groups having 1 to 8 carbon atoms. Specific examples of the alkynyl group include an ethynyl group and a propargyl group. At least one hydrogen atom in the alkynyl group may be substituted with an arbitrary substituent, for example. The substituent in the alkynyl group is not particularly limited, and examples thereof include those described above as examples of the substituent in the alkynyl group.

In the present invention, $X_2$ in the general formula (1) is a halogeno group, an amino group, a hydroxy group, an alkoxy group, a thio group (thiol group), or an alkylthio group. Preferably, $X_2$ is an amino group.

When $X_2$ is a halogeno group, the halogeno group is not particularly limited, and examples thereof include a fluoro group (fluorine atom), a chloro group (chlorine atom), a bromo group (bromine atom), and an iodo group (iodine atom). Among them, the chloro group (chlorine atom) is preferable.

When $X_2$ is an amino group, at least one hydrogen atom in the amino group may be substituted with a different substituent, for example. The substituent in the amino group is not particularly limited, and examples thereof include those described above as examples of the substituent in the amino group.

When $X_2$ is a hydroxy group, the hydroxy group may be present in the form of an oxo group (=O) as a result of isomerization, and the hydrogen atom therein may be substituted with an arbitrary substituent, for example. The substituent in the hydroxy group is not particularly limited, and examples thereof include those described above as examples of the substituent in the hydroxy group.

When $X_2$ is an alkoxy group, the alkoxy group is not particularly limited, and examples thereof include straight-chain or branched alkoxy groups having 1 to 8 carbon atoms. Specific examples of the alkoxy group include a methoxy group, an ethoxy group, a propoxy group, and a butoxy group. At least one hydrogen atom in the alkoxy group may be substituted with an arbitrary substituent, for example. The substituent in the alkoxy group is not particularly limited, and examples thereof include those described above as examples of the substituent in the alkoxy group.

When $X_2$ is a thio group (thiol group), a hydrogen atom in the thio group (thiol group) may be substituted with an arbitrary substituent, for example. The substituent in the thio group (thiol group) is not particularly limited, and examples thereof include those described above as examples of the substituent in the thio group (thiol group).

When $X_2$ is an alkylthio group, the alkylthio group is not particularly limited, and examples thereof include straight-chain or branched alkylthio groups having 1 to 8 carbon atoms. Specific examples of the alkylthio group include a methylthio group, an ethylthio group, an n-propylthio group, and an isopropylthio group. Among them, the methylthio group is preferable. At least one hydrogen atom in the alkylthio group may be substituted with an arbitrary substituent, for example. The substituent in the alkylthio group is not particularly limited, and examples thereof include those described above as examples of the substituent in the alkylthio group.

In the present invention, $X_3$ in the general formula (1) is a hydrogen atom, a halogeno group, or an alkoxy group.

When $X_3$ is a halogeno group, the halogeno group is not particularly limited, and examples thereof include a fluoro group (fluorine atom), a chloro group (chlorine atom), a bromo group (bromine atom), and an iodo group (iodine atom). Among them, the chloro group (chlorine atom) is preferable.

When $X_3$ is an alkoxy group, the alkoxy group is not particularly limited, and examples thereof include straight-chain or branched alkoxy groups having 1 to 8 carbon atoms. Specific examples of the alkoxy group include a methoxy group, an ethoxy group, a propoxy group, and a butoxy group. At least one hydrogen atom in the alkoxy group may be substituted with an arbitrary substituent, for example. The substituent in the alkoxy group is not particularly limited, and examples thereof include those described above as examples of the substituent in the alkoxy group.

In the present invention, $R_1$ and $R_2$ in the general formula (1) are the same or different, and are each independently a hydrogen atom, a halogeno group, a carboxyl group, an alkyl group, an acyl group, a carbamoyl group, an acyloxy group, a hydroxyalkyl group, an acyloxyalkyl group, an alkoxyalkyl group, a haloalkyl group, or a phosphonooxyalkyl group. Among them, the hydroxyalkyl group is preferable.

When at least one of $R_1$ and $R_2$ is a hydroxyalkyl group, the hydroxyalkyl group is not particularly limited, and examples thereof include straight-chain or branched hydroxyalkyl groups having 1 to 8 carbon atoms. Specific examples of the hydroxyalkyl group include a hydroxymethyl group, a hydroxyethyl group, a hydroxypropyl group, and a phosphonooxyalkyl group. Among them, the hydroxymethyl group is preferable. At least one hydrogen atom in the hydroxyalkyl group may be substituted with an arbitrary substituent, for example. The substituent in the hydroxyalkyl group is not particularly limited, and examples thereof include those described above as examples of the substituent in the hydroxyalkyl group.

When at least one of $R_1$ and $R_2$ is a halogeno group, the halogeno group is not particularly limited, and examples thereof include a fluoro group (fluorine atom), a chloro group (chlorine atom), a bromo group (bromine atom), and an iodo group (iodine atom).

When at least one of $R_1$ and $R_2$ is a carboxyl group, a hydrogen atom in the carboxyl group may be substituted with an arbitrary substituent, for example. The substituent in the carboxyl group is not particularly limited, and examples thereof include those described above as examples of the substituent in the carboxyl group.

When at least one of $R_1$ and $R_2$ is an alkyl group, the alkyl group is not particularly limited, and examples thereof include straight-chain or branched alkyl groups having 1 to 8 carbon atoms. Specific examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, and a tert-pentyl group. Furthermore, at least one hydrogen atom in the alkyl group may be substituted with an arbitrary substituent, for example. The substituent in the alkyl group is not particularly limited, and examples thereof include those described above as examples of the substituent in the alkyl group.

When at least one of $R_1$ and $R_2$ is an acyl group, the acyl group is not particularly limited, and examples thereof include straight-chain or branched acyl groups having 1 to 8 carbon atoms. Specific examples of the acyl group include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group. At least one hydrogen atom in the acyl group may be substituted with an arbitrary substituent, for example. The substituent in the acyl group is not particularly limited, and examples thereof include those described above as examples of the substituent in the acyl group.

When at least one of $R_1$ and $R_2$ is a carbamoyl group, at least one hydrogen atom in the carbamoyl group may be substituted with an arbitrary substituent, for example. The substituent in the carbamoyl group is not particularly limited, and examples thereof include those described above as examples of the substituent in the carbamoyl group. Specific examples of the carbamoyl group in which the hydrogen atom(s) is substituted with a substituent include the above-described substituted carbamoyl groups.

When at least one of $R_1$ and $R_2$ is an acyloxy group, the acyloxy group is not particularly limited, and examples thereof include straight-chain or branched acyloxy groups having 1 to 8 carbon atoms. Specific examples of the acyloxy group include an acetoxy group, a propionyloxy group, a butanoyloxy group, and a 3-chlorobutyryloxy group. At least one hydrogen atom in the acyloxy group may be substituted with an arbitrary substituent, for example. The substituent in the acyloxy group is not particularly limited, and examples thereof include those described above as examples of the substituent in the acyloxy group.

When at least one of $R_1$ and $R_2$ is an acyloxyalkyl group, the acyloxyalkyl group is not particularly limited, and examples thereof include straight-chain or branched acyloxyalkyl groups having 2 to 8 carbon atoms. Examples of the acyloxyalkyl group include the above-described alkyl groups substituted with the above-described acyloxy groups. Specific examples of the acyloxyalkyl group include an acetoxyethyl group, a propionyloxyethyl group, a butanoyloxyethyl group, and a 3-chlorobutyryloxyethyl group. At least one hydrogen atom in the acyloxyalkyl group may be substituted with an arbitrary substituent, for example. The substituent in the acyloxyalkyl group is not particularly limited, and examples thereof include those described above as examples of the substituent in the acyloxyalkyl group.

When at least one of $R_1$ and $R_2$ is an alkoxyalkyl group, the alkoxyalkyl group is not particularly limited, and examples thereof include straight-chain or branched alkoxyalkyl groups having 2 to 8 carbon atoms. Specific examples of the alkoxyalkyl group include the above-described alkyl groups substituted with alkoxy groups such as a methoxymethyl group, an ethoxymethyl group, a methoxyethyl group, an ethoxyethyl group, and a propoxyethyl group. At least one hydrogen atom in the alkoxyalkyl group may be substituted with an arbitrary substituent, for example. The substituent in the alkoxyalkyl group is not particularly limited, and examples thereof include those described above as examples of the substituent in the alkoxyalkyl group.

When at least one of $R_1$ and $R_2$ is a haloalkyl group, the haloalkyl group is not particularly limited, and examples thereof include straight-chain or branched haloalkyl groups having 1 to 8 carbon atoms. Specific examples of the haloalkyl group include alkyl groups substituted with the above-described halogeno groups such as a chloromethyl group, a chloroethyl group, a chlorobutyl group, a dichloromethyl group, a trifluoromethyl group, a bromomethyl group, a bromoethyl group, a fluoromethyl group, and a trifluoroethyl group.

When at least one of $R_1$ and $R_2$ is a phosphonooxyalkyl group, the phosphonooxyalkyl group is not particularly limited, and examples thereof include straight-chain or branched phosphonooxyalkyl groups having 1 to 8 carbon atoms. Specific examples of the phosphonooxyalkyl group include a phosphonooxymethy group, a phosphonooxyethyl group, and a phosphonooxypropyl group. At least one hydrogen atom in the phosphonooxyalkyl group may be substituted with an arbitrary substituent, for example. The substituent in the phosphonooxyalkyl group is not particularly limited, and examples thereof include those described above as examples of the substituent in the phosphonooxyalkyl group.

The cyclobutyl purine derivative, the tautomer or stereoisomer thereof, or the salt, solvate, or hydrate thereof according to the present invention may be such that, in the general formula (1), $X_1$ is a chloro group, $X_2$ is an amino group, and $R_1$ and $R_2$ are hydroxymethyl groups, for example. Examples of such a cyclobutyl purine derivative include 6-amino-2-chloro-9-[trans-trans-2,3-bis(hydroxymethyl)cyclobutyl]purine and 6-amino-2-thiomethoxy-9-[trans-trans-2,3-bis(hydroxymethyl)cyclobutyl]purine.

In the present invention, all the theoretically possible tautomers and stereoisomers of the cyclobutyl purine derivative represented by the general formula (1) fall within the scope of the present invention. In the present specification, the cyclobutyl purine derivative represented by the general formula (1) and all the tautomers and stereoisomers thereof hereinafter collectively may be referred to simply as the cyclobutyl purine derivative represented by the general formula (1).

In the present invention, salts of the cyclobutyl purine derivative represented by the general formula (1) are not particularly limited, and examples thereof include: alkali metal salts such as sodium salt and potassium salt; alkaline-earth metal salts such as calcium salt and magnesium salt; ammonium salts; aliphatic amine salts such as trimethylamine salt, triethylamine salt, cyclohexylamine salt, ethanolamine salt, diethanolamine salt, triethanolamine salt, and procaine salt; aralkylamine salts such as N,N-dibenzylethylenediamine; heterocyclic aromatic amine salts such as pyridine salt, picoline salt, quinoline salt, and isoquinoline salt; quaternary ammonium salts such as tetramethylammonium salt, tetraethylammonium salt, benzyltrimethylammonium salt, benzyltributylammonium salt, methyltrioctylammonium salt, and tetrabutylammonium salt; amino-acid salts such as arginine salt, lysine salt, aspartate, and glutamate; inorganic acid salts such as hydrochloride, sulfate, nitrate, phosphate, carbonate, hydrogencarbonate, and perchlorate; organic acid salts such as acetate, propionate, lactate, maleate, fumarate, tartrate, malate, citrate, and ascorbate; and sulfonates such as methanesulfonate, isethionate, benzenesulfonate, and p-toluenesulfonate. In the present invention, solvates and hydrates of the cyclobutyl purine derivative represented by the general formula (1) also fall within the scope of the present invention.

The method for producing the cyclobutyl purine derivative represented by the general formula (1) according to the present invention is not particularly limited, and may be as follows, for example.

Production Example 1

When $X_1$ is a halogeno group, the method for producing the cyclobutyl purine derivative represented by the general formula (1) is not particularly limited, and examples thereof include a production method including the following steps (a) and (b).

(a) First, a cyclobutanol derivative represented by the following general formula (3) is synthesized according to the method of Basacchi et al. (G. S. Basacchi, A. Braitman, C. W. Cianci, J. M. Clark, A. K. Field, M. E. Hagen, D. R. Hockstein, M. F. Malley, T. Mitt, W. A. Slusarchyk, J. E. Sundeen, B. J. Terry, A. V. Tuomari, E. R. Weaver, M. G. Young and R. Zahler, J. Med. Chem., 1991, 34, 1415) or the like.

(b) Next, a purine derivative represented by the following general formula (4) (where Halo denotes a halogeno group) is caused to react with the cyclobutanol derivative, and further, an appropriate substitution reaction is caused depending on the substituent of $X_2$. As a result, a compound in which $X_1$ is a halogeno group, represented by the following general formula (5) (where Halo denotes a halogeno group) is obtained. A solvent used for the reaction of the purine derivative is not particularly limited, and examples thereof include tetrahydrofuran (THF), diethyl ether, 1,4-dioxane, toluene, and dichloromethane. Among them, THF is preferable. The reaction temperature of the purine derivative is not particularly Limited, and is, for example, in the range from 30° C. to 100° C., preferably from 45° C. to 55° C. The reaction time of the purine derivative is not particularly limited, and is, for example, in the range from 5 to 50 hours, preferably from 12 to 1.8 hours. The substituent in the substitution reaction appropriate for the substituent of $X_2$ is not particularly limited, as long as it is any of the substituents described above as examples of $X_2$. Furthermore, the solvent, reaction temperature, and reaction time in the substitution reaction appropriate for the substituent of $X_2$ can be set as appropriate depending on the substituent, and are not particularly limited. For example, when the substituent of $X_2$ is an amino group, after the reaction of the purine derivative, methanol saturated with ammonia may be caused to react with the reaction product. Prior to these reactions, a protection reaction with respect to functional groups $R_1$ and $R_2$ may be conducted as appropriate, and after the protection reaction, reactions such as a deprotection reaction and a dehydration reaction may be caused as appropriate, for example.

The following reaction process scheme 1 shows the scheme of the step (b).

(Reaction process scheme 1)

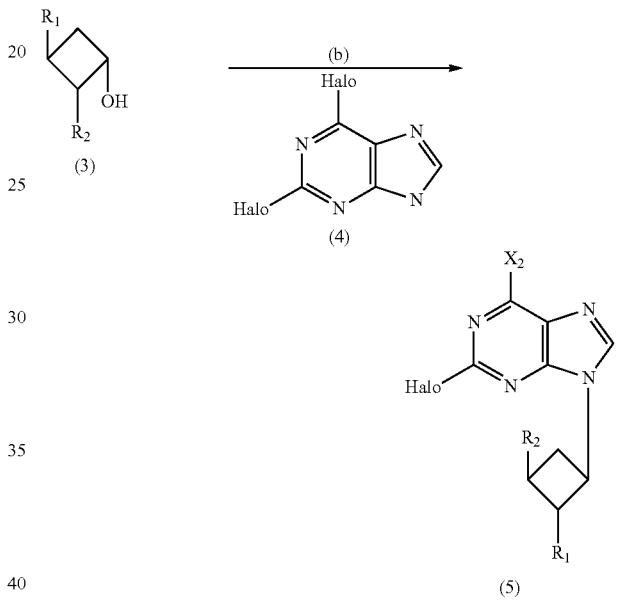

The cyclobutyl purine derivative produced according to the present production example is not particularly limited, and examples thereof include 6-amino-2-chloro-9-[trans-trans-2,3-bis(hydroxymethyl)cyclobutyl]purine ($C_{11}H_{14}ClN_5O_2$) represented by the following chemical formula (6).

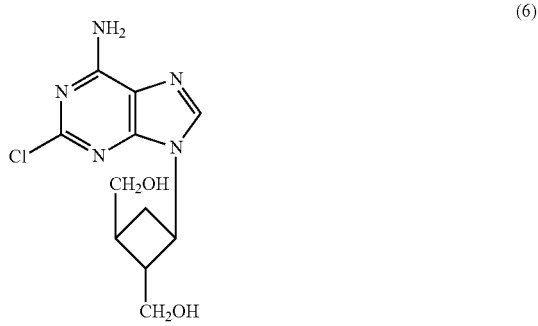 [SMILES: Nc1nc(Cl)nc2c1ncn2C1CC(CO)C1CO]

Production Example 2

In the method for producing the cyclobutyl purine derivative according to the present invention, $X_1$ may be introduced from the beginning as in Production Example 1. However, in the case where, for example, it is difficult to carry out the production method described in Production Example 1, a substituent different from the desired $X_1$ may be converted to $X_1$ after a coupling reaction. For example, when $X_1$ is an alkylthio group, the method for producing the cyclobutyl purine derivative represented by the general formula (1) is not particularly limited, and may be a production method including the steps described below, for example. The following reaction process scheme 2 shows the scheme of the present example. In the following reaction process scheme 2, Halo denotes a halogeno group and $R_3$ denotes an alkyl group.

(Reaction process scheme 2)

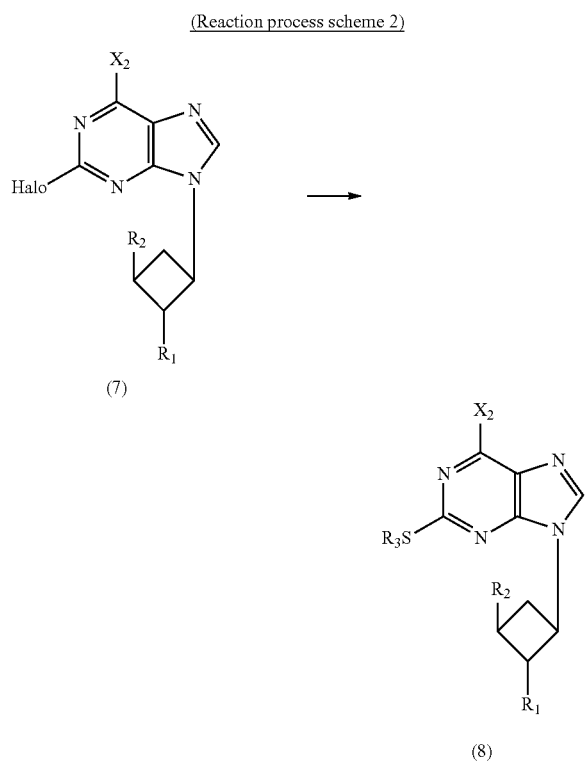

(7)

(8)

First, using the production method described in Production Example 1, a compound in which $X_1$ is a halogeno group, represented by the general formula (7) above is obtained. Then, the compound is caused to react with a thioalkylating agent in the presence of a solvent, whereby a compound represented by the general formula (8) (where $R_3$ is an alkyl group) is obtained. The thioalkylating agent is not particularly limited, and examples thereof include sodium thiomethoxide, sodium thioethoxide, and sodium thiophenoxide. Among them, sodium thiomethoxide is preferable. The solvent is not particularly limited, and examples thereof include N,N-dimethylformamide (DMF), dimethyl sulfoxide (DMSO), and 1,4-dioxane. Among them, DMF is preferable. The reaction temperature is not particularly limited, and is, for example, in the range from 10° C. to 80° C., preferably from 15° C. to 25° C. Furthermore, the reaction time is not particularly limited, and is, for example, in the range from 10 to 48 hours, preferably from 12 to 18 hours. Prior to the reaction, a protection reaction with respect to functional groups $R_1$ and $R_2$ may be conducted as appropriate, and after the protection reaction, reactions such as a deprotection reaction and a dehydration reaction may be caused as appropriate, for example.

The cyclobutyl purine derivative produced in the present production example is not particularly limited, and examples thereof include 6-amino-2-thiomethoxy-9-[trans-trans-2,3-bis(hydroxymethyl)cyclobutyl]purine ($C_{12}H_{17}N_5O_2S$) represented by the following chemical formula (9).

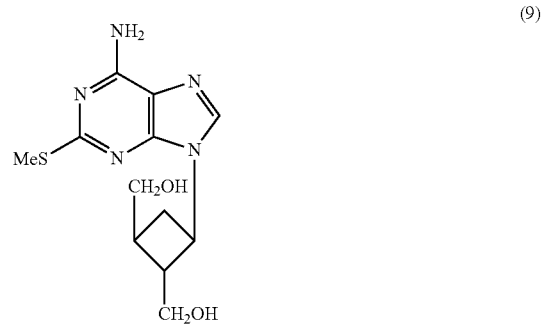 [SMILES: CSc1nc(N)c2ncn(C3CC(CO)C3CO)c2n1]

(9)

The method for producing the cyclobutyl purine derivative according to the present invention further may include, in addition to the steps described in the above-described production examples, other steps such as a separation step and a purification step of the reaction product obtained in each step, for example. The separation step and the purification step are not particularly limited, and conventionally known methods such as column chromatography and gel permeation chromatography can be used as appropriate, for example. As described above, the cyclobutyl purine derivative according to the present invention can be produced industrially, and besides, it has a low molecular weight. Therefore, the cyclobutyl purine derivative according to the present invention can be supplied stably at a low cost.

In the present invention, a method for producing a salt, a solvate, or a hydrate of the cyclobutyl purine derivative represented by the general formula (1) is not particularly limited, and they can be produced from a cyclobutyl purine derivative or the like obtained by any of the production methods illustrated in the above production examples or the like, using a conventionally known method as appropriate.

<Promoting Agent>

The promoting agent according to the present invention is, as described above, a promoting agent having at least one function selected from the group consisting of an angiogenesis-promoting function, a lumen formation-promoting function, and a neurocyte growth-promoting function, containing a cyclobutyl purine derivative represented by the general formula (1'), a tautomer or stereoisomer thereof, or a salt, solvate, or hydrate thereof.

In the present invention, $X_{1'}$ in the general formula (1') is a halogeno group, an alkyl group; an alkylthio group, a thio group (thiol group), an amino group, a hydroxy group, an alkoxy group, an alkynyl group, or a cyano group.

When $X_{1'}$ is a halogeno group, the halogeno group is not particularly limited, and examples thereof include a fluoro group (fluorine atom), a chloro group (chlorine atom), a bromo group (bromine atom), and an iodo group (iodine atom). Among them, the chloro group (chlorine atom) is preferable.

When $X_{1'}$ is an alkyl group, the alkyl group is not particularly limited, and examples thereof include straight-chain or branched alkyl groups having 1 to 8 carbon atoms. Specific examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, and a tert-pentyl group. Among them, the methyl group is preferable. At least one hydrogen atom in the alkyl group may be substituted with an arbitrary substituent, for example. The substituent in the alkyl group is not particularly Limited, and examples thereof include those described above as examples of the substituent in the alkyl group.

When $X_{1'}$ is an alkylthio group, the alkylthio group is not particularly limited, and examples thereof include straight-chain or branched alkylthio groups having 1 to 8 carbon atoms. Specific examples of the alkylthio group include a methylthio group, an ethylthio group, an n-propylthio group, and an isopropylthio group. Among them, the methylthio group is preferable. At least one hydrogen atom in the alkylthio group may be substituted with an arbitrary substituent, for example. The substituent in the alkylthio group is not particularly limited, and examples thereof include those described above as examples of the substituent in the alkylthio group.

When $X_{1'}$ is a thio group (thiol group), a hydrogen atom in the thio group (thiol group) may be substituted with an arbitrary substituent, for example. The substituent in the thio group (thiol group) is not particularly limited, and examples thereof include those described above as examples of the substituent in the thio group (thiol group).

When $X_{1'}$ is an amino group, at least one hydrogen atom in the amino group may be substituted with an arbitrary substituent, for example, and the amino group is not particularly limited. The substituent in the amino group is not particularly limited, and examples thereof include those described above as examples of the substituent in the amino group.

When $X_{1'}$ is a hydroxy group, the hydroxy group may be present in the form of an oxo group (=O) as a result of isomerization, and the hydrogen atom therein may be substituted with an arbitrary substituent, for example. The substituent in the hydroxy group is not particularly limited, and examples thereof include those described above as examples of the substituent in the hydroxy group.

When $X_{1'}$ is an alkoxy group, the alkoxy group is not particularly limited, and examples thereof include straight-chain or branched alkoxy groups having 1 to 8 carbon atoms. Specific examples of the alkoxy group include a methoxy group, an ethoxy group, a propoxy group, and a butoxy group. At least one hydrogen atom in the alkoxy group may be substituted with an arbitrary substituent, for example. The substituent in the alkoxy group is not particularly limited, and examples thereof include those described above as examples of the substituent in the alkoxy group.

When $X_{1'}$ is an alkynyl group, the alkynyl group is not particularly limited, and examples thereof include straight-chain or branched alkynyl groups having 1 to 8 carbon atoms. Specific examples of the alkynyl group include an ethynyl group and a propargyl group. At least one hydrogen atom in the alkynyl group may be substituted with an arbitrary substituent, for example. The substituent in the alkynyl group is not particularly limited, and examples thereof include those described above as examples of the substituent in the alkynyl group.

In the general formula (1'),
$X_{2'}$ is a halogeno group, an amino group, a hydroxy group, an alkoxy group, a thio group (thiol group), or an alkylthio group.

When $X_{2'}$ is a halogeno group, the halogeno group is not particularly limited, and examples thereof include a fluoro group (fluorine atom), a chloro group (chlorine atom), a bromo group (bromine atom), and an iodo group (iodine atom). Among them, the chloro group (chlorine atom) is preferable.

When $X_{2'}$ is an amino group, at least one hydrogen atom in the amino group may be substituted with an arbitrary substituent, for example, and the amino group is not particularly limited. The substituent in the amino group is not particularly limited, and examples thereof include those described above as examples of the substituent in the amino group.

When $X_{2'}$ is a hydroxy group, the hydroxy group may be present in the form of an oxo group (=O) as a result of isomerization, and the hydrogen atom therein may be substituted with an arbitrary substituent, for example. The substituent in the hydroxy group is not particularly limited, and examples thereof include those described above as examples of the substituent in the hydroxy group.

When $X_{2'}$ is an alkoxy group, the alkoxy group is not particularly limited, and examples thereof include straight-chain or branched alkoxy groups having 1 to 8 carbon atoms. Specific examples of the alkoxy group include a methoxy group, an ethoxy group, a propoxy group, and a butoxy group. At least one hydrogen atom in the alkoxy group may be substituted with an arbitrary substituent, for example. The substituent in the alkoxy group is not particularly limited, and examples thereof include those described above as examples of the substituent in the alkoxy group.

When $X_{2'}$ is a thio group (thiol group), a hydrogen atom in the thio group (thiol group) may be substituted with an arbitrary substituent, for example. The substituent in the thio group (thiol group) is not particularly limited, and examples thereof include those described above as examples of the substituent in the thio group (thiol group).

When $X_{2'}$ is an alkylthio group, the alkylthio group is not particularly limited, and examples thereof include straight-chain or branched alkylthio groups having 1 to 8 carbon atoms. Specific examples of the alkylthio group include a methylthio group, an ethylthio group, an n-propylthio group, and an isopropylthio group. Among them, the methylthio group is preferable. At least one hydrogen atom in the alkylthio group may be substituted with an arbitrary substituent, for example. The substituent in the alkylthio group is not particularly limited, and examples thereof include those described above as examples of the substituent in the alkylthio group.

In the present invention, $X_{3'}$ in the general formula (1') is a hydrogen atom, a halogeno group, an alkyl group, an alkylthio group, an amino group, a hydroxy group, an alkoxy group, a hydroxyphenyl group, or a carbamoyl group.

When $X_{3'}$ is a halogeno group, the halogeno group is not particularly limited, and examples thereof include a fluoro group (fluorine atom), a chloro group (chlorine atom), a bromo group (bromine atom), and an iodo group (iodine atom).

When $X_{3'}$ is an alkyl group, the alkyl group is not particularly limited, and examples thereof include straight-chain or branched alkyl groups having 1 to 8 carbon atoms. Specific examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, and a tert-pentyl group. Among them, the methyl group is preferable. At least one hydrogen atom in the alkyl group may be substituted with an arbitrary substituent, for example. The substituent in the alkyl group is not particularly limited, and examples thereof include those described above as examples of the substituent in the alkyl group.

When $X_{3'}$ is an alkylthio group, the alkylthio group is not particularly limited, and examples thereof include straight-chain or branched alkylthio groups having 1 to 8 carbon atoms. Specific examples of the alkylthio group include a methylthio group, an ethylthio group, an n-propylthio group, and an isopropylthio group. At least one hydrogen atom in the alkylthio group may be substituted with an arbitrary substituent, for example. The substituent in the alkylthio group is not particularly limited, and examples thereof include those described above as examples of the substituent in the alkylthio group.

When $X_{3'}$ is an amino group, at least one hydrogen atom in the amino group may be substituted with an arbitrary substituent, for example. The substituent in the amino group is not particularly limited, and examples thereof include those described above as examples of the substituent in the amino group.

When $X_{3'}$ is a hydroxy group, the hydroxy group may be present in the form of an oxo group (=O) as a result of isomerization, and the hydrogen atom therein may be substituted with an arbitrary substituent, for example. The substituent in the hydroxy group is not particularly limited, and examples thereof include those described above as examples of the substituent in the hydroxy group.

When $X_{3'}$ is an alkoxy group, the alkoxy group is not particularly limited, and examples thereof include straight-chain or branched alkoxy groups having 1 to 8 carbon atoms. Specific examples of the alkoxy group include a methoxy group, an ethoxy group, a propoxy group, and a butoxy group. At least one hydrogen atom in the alkoxy group may be substituted with an arbitrary substituent, for example. The substituent in the alkoxy group is not particularly limited, and examples thereof include those described above as examples of the substituent in the alkoxy group.

When $X_{3'}$ is a hydroxyphenyl group, a hydroxy group in the hydroxyphenyl group may be present in the form of an oxo group (=O) as a result of isomerization, and the hydrogen atom therein may be substituted with an arbitrary substituent, for example. The substituent in the hydroxyphenyl group encompasses those that can be deprotected with acid, and is not particularly limited. Examples of the substituent include those described above as examples of the substituent in the hydroxyphenyl group.

When $X_{3'}$ is a carbamoyl group, at least one hydrogen atom in the carbamoyl group may be substituted with an arbitrary substituent, for example. The substituent in the carbamoyl group is not particularly limited, and examples thereof include those described above as examples of the substituent in the carbamoyl group. Specific examples of the carbamoyl group in which the hydrogen atom(s) is substituted with a substituent include the above-described substituted carbamoyl groups.

$R_{1'}$ and $R_{2'}$ in the general formula (1') are the same or different, and are each independently a hydrogen atom, a halogeno group, a carboxyl group, an alkyl group, an acyl group, a carbamoyl group, an acyloxy group, a hydroxyalkyl group, an acyloxyalkyl group, an alkoxyalkyl group, a haloalkyl group, or a phosphonooxyalkyl group.

When at least one of $R_{1'}$ and $R_{2'}$ is a halogeno group, the halogeno group is not particularly limited, and examples thereof include a fluoro group (fluorine atom), a chloro group (chlorine atom), a bromo group (bromine atom), and an iodo group (iodine atom).

When at least one of $R_{1'}$ and $R_{2'}$ is a carboxyl group, a hydrogen atom in the carboxyl group may be substituted with an arbitrary substituent, for example. The substituent in the carboxyl group is not particularly limited, and examples thereof include those described above as examples of the substituent in the carboxyl group.

When at least one of $R_{1'}$ and $R_{2'}$ is an alkyl group, the alkyl group is not particularly limited, and examples thereof include straight-chain or branched alkyl groups having 1 to 8 carbon atoms. Specific examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, and a tert-pentyl group. Among them, the methyl group is preferable. At least one hydrogen atom in the alkyl group may be substituted with an arbitrary substituent, for example. The substituent in the alkyl group is not particularly limited, and examples thereof include those described above as examples of the substituent in the alkyl group.

When at least one of $R_{1'}$ and $R_{2'}$ is an acyl group, the acyl group is not particularly limited, and examples thereof include straight-chain or branched acyl groups having 1 to 8 carbon atoms. Specific examples of the acyl group include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group. At least one hydrogen atom in the acyl group may be substituted with an arbitrary substituent, for example. The substituent in the acyl group is not particularly limited, and examples thereof include those described above as examples of the substituent in the acyl group.

When at least one of $R_{1'}$ and $R_{2'}$ is a carbamoyl group, at least one hydrogen atom in the carbamoyl group may be substituted with an arbitrary substituent, for example. The substituent in the carbamoyl group is not particularly limited, and examples thereof include those described above as examples of the substituent in the carbamoyl group. Specific examples of the carbamoyl group in which the hydrogen atom(s) is substituted with a substituent include the above-described substituted carbamoyl groups.

When at least one of $R_{1'}$ and $R_{2'}$ is an acyloxy group, the acyloxy group is not particularly limited, and examples thereof include straight-chain or branched acyloxy groups having 1 to 8 carbon atoms. Specific examples of the acyloxy group include an acetoxy group, a propionyloxy group, a butanoyloxy group, and a 3-chlorobutyryloxy group. At least one hydrogen atom in the acyloxy group may be substituted with an arbitrary substituent, for example. The substituent in the acyloxy group is not particularly limited, and examples thereof include those described above as examples of the substituent in the acyloxy group.

When at least one of $R_{1'}$ and is a hydroxyalkyl group, the hydroxyalkyl group is not particularly limited, and examples thereof include straight-chain or branched hydroxyalkyl groups having 1 to 8 carbon atoms. Specific examples of the hydroxyalkyl group include a hydroxymethyl group, a hydroxyethyl group, and a hydroxypropyl group. Among them, the hydroxymethyl group is preferable. At least one hydrogen atom in the hydroxyalkyl group may be substituted with an arbitrary substituent, for example. The substituent in the hydroxyalkyl group is not particularly limited, and examples thereof include those described above as examples of the substituent in the hydroxyalkyl group.

When at least one of $R_{1'}$ and $R_{2'}$ is an acyloxyalkyl group, the acyloxyalkyl group is not particularly limited, and examples thereof include straight-chain or branched acyloxyalkyl groups having 2 to 8 carbon atoms. Examples of the acyloxyalkyl group include the above-described alkyl groups substituted with the above-described acyloxy groups. Specific examples of the acyloxyalkyl group include an acetoxyethyl group, a propionyloxyethyl group, a butanoyloxyethyl group, and a 3-chlorobutyryloxyethyl group. At least one hydrogen atom in the acyloxyalkyl group may be substituted with an arbitrary substituent, for example. The substituent in the acyloxyalkyl group is not particularly limited, and examples thereof include those described above as examples of the substituent in the acyloxyalkyl group.

When at least one of $R_{1'}$ and $R_{2'}$ is an alkoxyalkyl group, the alkoxyalkyl group is not particularly limited, and examples thereof include straight-chain or branched alkoxyalkyl groups having 2 to 8 carbon atoms. Specific examples of the alkoxyalkyl group include the above-described alkyl groups substituted with alkoxy groups such as a methoxymethyl group, an ethoxymethyl group, a methoxyethyl group, an ethoxyethyl group, and a propoxyethyl group. At least one hydrogen atom in the alkoxyalkyl group may be substituted with an arbitrary substituent, for example. The substituent in the alkoxyalkyl group is not particularly limited, and examples thereof include those described above as examples of the substituent in the alkoxyalkyl group.

When at least one of $R_{1'}$ and $R_{2'}$ is a haloalkyl group, the haloalkyl group is not particularly limited, and examples thereof include straight-chain or branched haloalkyl groups having 1 to 8 carbon atoms. Specific examples of the haloalkyl group include alkyl groups substituted with the halogeno groups such as a chloromethyl group, a chloroethyl group, a chlorobutyl group, a dichloromethyl group, a trifluoromethyl group, a bromomethyl group, a bromoethyl group, a fluoromethyl group, and a trifluoroethyl group.

When at least one of $R_{1'}$ and $R_{2'}$ is a phosphonooxyalkyl group, the phosphonooxyalkyl group is not particularly limited, and examples thereof include straight-chain or branched phosphonooxyalkyl groups having 1 to 8 carbon atoms. Specific examples of the phosphonooxyalkyl group include a phosphonooxymethy group, a phosphonooxyethyl group, and a phosphonooxypropyl group. At least one hydrogen atom in the phosphonooxyalkyl group may be substituted with an arbitrary substituent, for example. The substituent in the phosphonooxyalkyl group is not particularly limited, and examples thereof include those described above as examples of the substituent in the phosphonooxyalkyl group.

When $X_{1'}$ is an amino group and $X_{3'}$ is a hydrogen atom, $R_{1'}$ and $R_{2'}$ are each independently an atom or substituent other than a hydroxyalkyl group.

The promoting agent according to the present invention may be such that, in the general formula (1'), $X_{1'}$ is a chloro group, $X_{2'}$ is an amino group, and $R_{1'}$ and $R_{2'}$ are hydroxymethyl groups, for example. Examples of such a promoting agent include promoting agents having at least one function selected from the group consisting of an angiogenesis-promoting function, a lumen formation-promoting function, and a neurocyte growth-promoting function, containing 6-amino-2-chloro-9-[trans-trans-2,3-bis (hydroxymethyl)cyclobutyl]purine or 6-amino-2-thiomethoxy-9-[trans-trans-2,3-bis(hydroxymethyl)cyclobutyl]purine, a tautomer or stereoisomer thereof, or a salt, solvate, or hydrate thereof.

In the present invention, promoting agents having at least one function selected from the group consisting of an angiogenesis-promoting function, a lumen formation-promoting function, and a neurocyte growth-promoting function, containing any of all the theoretically possible tautomers and stereoisomers of the cyclobutyl purine derivative represented by the general formula (1') of the present invention fall within the scope of the present invention. In the present specification, the cyclobutyl purine derivative represented by the general formula (1') and all the tautomers and stereoisomers thereof hereinafter collectively may be referred to simply as the cyclobutyl purine derivative represented by the general formula (1').

In the present invention, a salt of the cyclobutyl purine derivative represented by the general formula (1') is not particularly limited, and examples thereof include those described above as examples of salts of the cyclobutyl purine derivative represented by the general formula (1). Furthermore, in the present invention, promoting agents having at least one function selected from the group consisting of an angiogenesis-promoting function, a lumen formation-promoting function, and a neurocyte growth-promoting function, containing any of salts, solvates, and hydrates of the cyclobutyl purine derivative represented by the general formula (1') also fall within the scope of the present invention.

A method for producing the cyclobutyl purine derivative represented by the general formula (1') according to the present invention is not particularly limited, and examples thereof include those described above as examples of a method for producing the cyclobutyl purine derivative represented by the general formula (1). In the present invention, a method for producing a salt, a solvate, or a hydrate of the cyclobutyl purine derivative represented by the general formula (1') also is not particularly limited, and they can be produced from a cyclobutyl purine derivative or the like obtained by any of the production methods of the cyclobutyl purine derivative represented by the general formula (1) or the like, using a conventionally known method as appropriate.

The promoting agent according to the present invention is, as described above, a promoting agent having at least one function selected from the group consisting of an angiogenesis-promoting function, a lumen formation-promoting function, and a neurocyte growth-promoting function. Specifically, the promoting agent is an angiogenesis promoting agent, a lumen formation promoting agent, a neurocyte growth promoting agent, or the like, for example. The angiogenesis promoting agent has a function of promoting angiogenesis, and it may have, for example, a function of promoting proliferation of vascular endothelial cells, a function of promoting the migration of vascular endothelial cells, or the like. The lumen formation promoting agent is not particularly limited, and is, for example, an agent for promoting lumen formation by vascular endothelial cells, an agent for promoting lumen formation by digestive tract-derived cells, an agent for promoting lumen formation by liver-derived cells, an agent for prompting lymphangiogenesis, or the like. Among them, the agent for promoting lumen formation by vascular endothelial cells is preferable. The neurocyte growth promoting agent is not particularly limited, and is, for example, a neurocyte proliferation-promoting agent, a neurocyte differentiation-promoting agent, or the like. Among them, the neurocyte proliferation-promoting agent is preferable. Although the promoting agent according to the present invention has at least one function selected from the group consisting of the angiogenesis-promoting function, the lumen formation-promoting function, and the neurocyte growth-promoting function, it also may have a function(s) other than the angiogenesis-promoting function, the lumen formation-promoting function, and the neurocyte growth promoting function at the same time. The other function(s) of the promoting agent according to the present invention is not particularly limited.

<Drug>

The drug according to the present invention is, as described above, a drug for use in at least one selected from the group consisting of promoting angiogenesis, promoting lumen formation, and promoting neurocyte growth, containing at least one selected from the group consisting of the cyclobutyl purine derivative, the tautomers and stereoisomers thereof, the salts, solvates, and hydrates thereof according to the present invention, and the promoting agent according to the present invention. In the present invention, the term "drug" encompasses drugs and quasi drugs. The drug according to the present invention is not particularly limited, and examples thereof include: wound healing agents such as a therapeutic agent for injury, a therapeutic agent for burn, a therapeutic agent for scar, and a therapeutic agent for decubitus; therapeutic agents for Alzheimer's disease; prophylactic agents for Alzheimer's disease; therapeutic agents for infarction diseases; prophylactic agents for infarction diseases; and hair growth agents.

The drug according to the present invention can be administered orally or parenterally. In the case of oral administration, the dosage form of the drug of the present invention is not particularly limited, and examples thereof include powder medicines, microgranules, granules, tablets, coated tablets, capsules, troches, and liquid medicines. In the case of parenteral administration, the dosage form of the drug of the present invention is not particularly limited, and examples thereof include injections, nasal drops, ointments, patches, cataplasms, lotions, and suppositories. Furthermore, the composition of the drug is not particularly limited. For example, in addition to the promoting agent, the drug may contain various additives such as an excipient, a binding agent, a lubricant, a disintegrant, an absorption promoter, an emulsifying agent, a stabilizing agent, and an antiseptic agent. The drug can be produced according to a commonly used drug production technique or the like.

In the drug according to the present invention, the dose of the cyclobutyl purine derivative according to the present invention can be set as appropriate depending on the dosage form, the administration method, the target disease, the patient to whom the drug is administered, and the like, and is not particularly limited.

EXAMPLES

Hereinafter, examples of the present invention will be described. It is to be noted, however, the present invention is by no means limited or restricted by the following examples.

Example 1

In the present example, the effect of 6-amino-2-chloro-9-[trans-trans-2,3-bis(hydroxymethyl)cyclobutyl]purine ($C_{11}H_{14}ClN_5O_2$, hereinafter referred to as "2-Cl-C.OXT-A") represented by the above chemical formula (6) on the cell proliferation, lumen formation, and cell migration of vascular endothelial cells was examined.

<Synthesis of 2-Cl-C.OXT-A>

The 2-Cl-C.OXT-A was synthesized by the following steps 1 to 3. In the present example, $^1$H NMR and $^{13}$C NMR spectra were measured using Ultrashield™ 400 Plus FT NMR System (BRUKER). The chemical shift was denoted by δ, and the coupling constant (J) was denoted by Hz. The melting point was measured using a micro melting point measuring system MP-500D (Yanaco Kiki Kaihatsu Kenkyujo). Elementary analysis was carried out using a 2400 Series II CHNS/O (Perkin Elmer). High-resolution mass spectrometry was carried out according to electrospray ionization mass spectrometry (ESI-MS) using an APEX IV mass spectrometer (BRUKER).

(Step 1: Synthesis of cis-trans-2,3-bis(benzoyloxymethyl)-1-cyclobutanol)

In the present example, cis-trans-2,3-bis(benzoyloxymethyl)-1-cyclobutanol was synthesized in the following manner based on the method of Basacchi et al. (G. S. Basacchi, A. Braitman, C. W. Cianci, J. M. Clark, A. K. Field, M. E. Hagen, D. R. Hockstein, M. F. Malley, T. Mitt, W. A. Slusarchyk, J. E. Sundeen, B. J. Terry, A. V. Tuomari, E. R. Weaver, M. G. Young and R. Zahler, J. Med. Chem., 1991, 34, 1415). First, 14.00 g (41.40 mmol) of trans-2,3-bis(benzoyloxymethyl)-1-cyclobutanone was dissolved in 350 ml of dry THF, and the resultant solution was cooled to −78° C. in a nitrogen stream. After the cooling, 42 ml of 1 mmol/l LS-selectride THF solution was dripped into the solution while stirring, and 2 hours later. 6 ml of acetic acid was further dripped thereto. The resultant solution was allowed to stand still until it reached room temperature, and thereafter, it was concentrated to 20 ml. 250 ml of toluene and 100 ml of water were added to the concentrate, and the resultant solution was shaken in a separating funnel. The organic layer obtained was washed with 100 ml of water and then dried using magnesium sulfate. After the drying, solids were removed by filtration, and the filtrate was concentrated to 20 ml. This concentrate (liquid residue) was separated by chromatography using a silica gel column. Thus, viscous syrup-like cis-trans-2,3-bis(benzoyloxymethyl)-1-cyclobutanol (10.15 g, yield: 72%) was obtained.

(Step 2: Synthesis of 2,6-dichloro-9-[trans-trans-2,3-bis(benzoyloxymethyl)cyclobutyl]purine)

Next, the cis-trans-2,3-bis(benzoyloxymethyl)-1-cyclobutanol (5.20 g, 15.28 mmol) and 2,6-dichloro purine (4.33 g, 22.9 mmol) were dissolved in 100 ml of THF. While cooling the resultant solution with ice, triphenylphosphine (7.87 g, 30 mmol) was added thereto. Thereafter, diisopropyl azodicarboxylate (5.9 ml, 30 mmol) was added further, and the resultant solution was kept at 50° C. overnight. This solution was concentrated, and then, the liquid residue was separated by chromatography using a silica gel column. Thus, white crystals of 2,6-dichloro-9-[trans-trans-2,3-bis(benzoyloxymethyl)cyclobutyl]purine represented by the following chemical formula (10) (4.44 g, yield: 57%) were obtained.

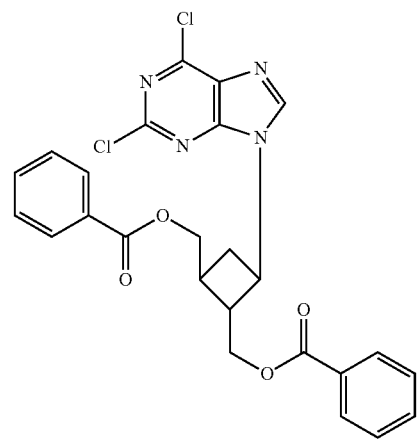

(10)

Physical properties of this compound are shown below.

Mp: 146.8° C. to 147.4° C., MS m/z=510, 512, 514 (M$^+$). HR-MS. calcd. for $C_{25}H_{20}Cl_2N_4O_4$: 510.0862. Found; 510.0846. Anal. Calc. for $C_{23}H_{20}Cl_2N_4O_4 \cdot 0.3H_2O.C$, 58.11; H, 4.02; N, 10.84. Found. C, 57.79; H, 3.94; N, 10.87.

(Step 3: Synthesis of 6-amino-2-chloro-9-[trans-trans-2,3-bis (hydroxymethyl)cyclobutyl]purine)

The 2,6-dichloro-9-[trans-trans-2,3-bis(benzoyloxymethyl)cyclobutyl]purine (3.73 g, 7.29 mmol) was suspended in 50 ml of MeOH, and saturated with ammonia. This solution was heated to 100° C. overnight in a 200 ml sealed steel tube. After completion of the heating, the solution was cooled with ice, and the solvent was evaporated under reduced pressure using an evaporator. To the residual substance obtained, 50 ml of water was added, and the resultant solution was washed twice with 30 ml of $CHCl_3$. After the washing, the aqueous layer was collected and concentrated to 10 ml. Thus, white crystals of 6-amino-2-chloro-9-[trans-trans-2,3-bis (hydroxymethyl)cyclobutyl]purine (2-Cl-C.OXT-A) represented by the chemical formula (6) (1.49 g, 72%) were obtained. Physical properties of this compound are shown below.

$^1$H NMR (400 MHz, DMSO-$d_6$): δ 8.25 (1H, s), 7.68 (2H, br s), 4.63 (1H, dd, J 5.2 and 4.6), 4.53-4.60 (2H, m), 3.46-3.56 (4H, m), 2.72-2.82 (1H, m), 2.38-2.46 (1H, m), 2.14 (1H, dd, J 19.2 and 9.6), 2.03-2.12 (1H, m); $^{13}$C NMR (100 MHz, DMSO-$d_6$): δ156.7, 152.6, 150.4, 140.2, 118.0, 63.5, 61.4, 47.6, 47.3, 33.0, 29.4. Mp 172° C. to 173.5° C. Anal. calcd. for $C_{11}H_{14}ClN_5O_2 \cdot 0.2H_2O$.C, 45.98; H, 5.05; N, 24.37. Found. C, 45.83; H, 5.01; N, 24.23.

<Measurement of Cell Proliferation>

Sample solutions were prepared by dissolving 2-Cl-C.OXT-A in physiological saline so as to achieve predetermined concentrations (0.5, 1, 5, 10, 50, 100 mmol/l). Then, the sample solutions containing 2-Cl-C.OXT-A at the predetermined concentrations respectively were added to HuMedia-EB2 media (Kurabo) to which 2 v/v % inactivated fetal bovine serum (FBS) had been added so that their concentrations became 10 v/v %. Thus, cell proliferation media were prepared. The final concentrations of 2-Cl-C.OXT-A in the cell proliferation media were 50, 100, 500 μmol/l, 1, 5, and 10 mmol/l.

Human umbilical vein endothelial cells (HUVEC) suspended in a HuMedia-EG2 medium (Kurabo) were inoculated into each of gelatin-coated wells of a 96-well plate at a density of 3×10$^3$ cells per well, and cultured for 24 hours. 24 hours after the start of the culture, the medium was removed, and 100 μl of the cell proliferation medium was added to each well. The cells were cultured for another 48 hours. After the completion of the culture, a color reaction was caused using a Cell Counting Kit-8 (Dojindo Laboratories). 2 hours after the start of the reaction, the absorbance at 450 nm was measured using a microplate reader. As a control, a HuMedia-EB2 medium (Kurabo) to which 2 v/v % inactivated fetal bovine serum (FBS) had been added was used instead of the cell proliferation medium to carry out the culture, and a color reaction was caused and the absorbance was measured in the same manner as in the above. Then, using the following equation (I), the relative absorbance in the culture using each of the cell proliferation media containing 2-Cl-C.OXT-A at the predetermined concentrations was calculated.

$$\text{Relative absorbance} = \frac{\text{Absorbance in culture using medium containing 2-Cl—C•OXT-A}}{\text{Absorbance in control}} \quad (I)$$

<Measurement of Lumen Formation>

The measurement of lumen formation was carried out in the following manner using commercially available angiogenesis kits (Kurabo), each including human umbilical vein endothelial cells (HUVEC) and normal human dermal fibroblasts. First, sample solutions were prepared by dissolving 2-Cl-C.OXT-A in physiological saline so as to achieve predetermined concentrations (1, 10, 100, 500 μmol/l, 1, 5, 10, 50 mmol/l). Then, the sample solutions containing 2-Cl-C.OXT-A at the predetermined concentrations respectively were added to media provided in the kits so that their concentrations became 10 v/v %. Thus, lumen formation media were prepared. The final concentrations of 2-Cl-C.OXT-A in the lumen formation media were 0.1, 1, 10, 50, 100, 500 μmol/l, 1 and 5 mmol/l.

Using each of the lumen formation media, the human umbilical vein endothelial cells (HUVEC) and the normal human dermal fibroblasts were cultured for 10 days. After the culture, the human umbilical vein endothelial cells (HUVEC) were immunostained using a lumen staining kit (for CD31 staining, Kurabo). Then, using NIH Image (image processing and analysis software), the area of a portion stained by the immunostaining (lumen area) was measured. As a control, a medium provided in the kit was used instead of the lumen formation medium to carry out the culture, and the cells were immunostained and the lumen area was measured in the same manner as in the above. Then, using the following equation (II), the relative value of lumen area in the culture using each of the lumen formation media containing 2-Cl-C.OXT-A at the predetermined concentrations was calculated.

$$\text{Relative value of lumen area} = \frac{\text{Lumen area in culture using medium containing 2-Cl—C•OXT-A}}{\text{Lumen area in control}} \quad (II)$$

<Measurement of Cell Migration>

Measurement of cell migration was carried out in the following manner using CytoSelect 24-well Cell Migration Assay (CBA-100, Cell Biolabs) kits. First, sample solutions were prepared by dissolving 2-Cl-C.OXT-A in physiological saline so as to achieve predetermined concentrations (0.1, 0.5, 1 mmol/l). Then, the sample solutions containing 2-Cl-C.OXT-A at the predetermined concentrations respectively were added to HuMedia-EB2 media (Kurabo) to which 2 v/v % inactivated fetal bovine serum (FBS) had been added so that their concentrations became 10 v/v %. Thus, cell migration media were prepared. The final concentrations of 2-Cl-C.OXT-A in the cell migration media were 10, 50, and 100 μmol/l.

Human umbilical vein endothelial cells (HUVEC) were suspended in a HuMedia-EB2 medium (Kurabo) to which 2 v/v % inactivated fetal bovine serum (FBS) had been added at a density of 0.5×10$^6$ cells/ml. Thus, a cell suspension was prepared. 300 μl of the cell suspension was added to an upper compartment (i.e., in an insert) of a polycarbonate membrane plate provided in the kit, and 500 μl of the cell migration medium was added to a lower compartment (i.e., in a well) of the plate. Then, the cells were cultured at 37° C. for 24 hours. After the completion of the culture, the membrane on the inner bottom face of the insert was wiped out with a cotton swab to remove the cells on the membrane. Then, cells having migrated to the rear face of the membrane (the membrane on the outer bottom face of the insert) were stained using a staining solution provided in the kit, and then photographed from below the insert. After the photographing, the dye was extracted with an extracting solution provided in the kit, and the absorbance at 560 nm was measured using a microplate reader. As a control, a HuMedia-EB2 medium (Kurabo) to which 2 v/v % inactivated fetal bovine serum (FBS) had been added was used instead of the cell migration medium to carry out the culture, and the cells were stained and the absorbance was measured in the same manner as in the above. Then, using the above equation (I), the relative absorbance in the culture using each of the cell migration media containing 2-Cl-C.OXT-A at the predetermined concentrations was calculated.

Comparative Example 1

In the present example, the effect of 6-amino-9-[trans-trans-2,3-bis(hydroxymethyl)cyclobutyl]purine (hereinafter referred to as "C.OXT-A") represented by the following chemical formula (11) on the lumen formation by vascular endothelial cells was examined. The lumen formation was measured in the same manner as in Example 1, except that the C.OXT-A was used instead of 2-Cl-C.OXT-A and the final concentrations of the C.OXT-A in the lumen formation media were set to 1, 5, 10, 50, and 100 µmol/l.

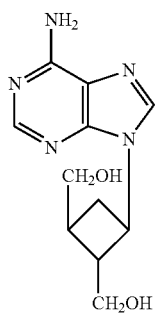

(11)

Comparative Example 2

In the present example, the effect of 2-amino-9-[trans-trans-2,3-bis(hydroxymethyl)cyclobutyl]-3H-purine-6-one (hereinafter referred to as "C.OXT-G") represented by the following chemical formula (12) on the lumen formation by vascular endothelial cells was examined. The lumen formation was measured in the same manner as in Example 1, except that the C.OXT-G was used instead of 2-Cl-C.OXT-A and the final concentrations of the C.OXT-G in the lumen formation media were set to 1, 5, 10, 50, and 100 µmol/l.

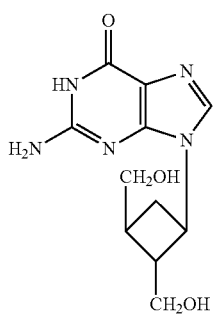

(12)

Comparative Example 3

In the present example, the effect of 2-chloro-6-amino-9-[3,4-dihydroxy-5-(hydroxymethyl)oxolane-2-yl]purine (hereinafter referred to as "2-Cl-ADN") represented by the following chemical formula (13) on the lumen formation by vascular endothelial cells was examined. The lumen formation was measured in the same manner as in Example 1, except that the 2-Cl-ADN was used instead of 2-Cl-C.OXT-A and the final concentrations of the 2-Cl-ADN in the lumen formation media were set to 500 nmol/l, 1, 5, and 10 µmol/l.

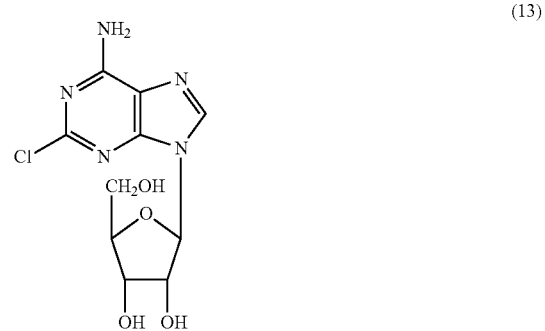 [SMILES: Nc1nc(Cl)nc2c1ncn2C1OC(CO)C(O)C1O]

(13)

Comparative Example 4

In the present example, the effect of 2-chloro-6-amino-9-[4-hydroxy-5-(hydroxymethyl)oxolane-2-yl]purine (hereinafter referred to as "2-Cl-DAD") represented by the following chemical formula (14) on the lumen formation by vascular endothelial cells was examined. The lumen formation was measured in the same manner as in Example 1, except that the 2-Cl-DAD was used instead of 2-Cl-C.OXT-A and the final concentrations of the 2-Cl-DAD in the lumen formation media were set to 500 nmol/l, 1, 5, and 10 µmol/l.

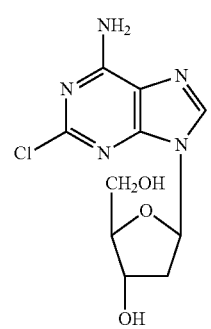

(14)

Comparative Example 5

In the present example, the effect of adenosine on the lumen formation by vascular endothelial cells was examined. The lumen formation was measured in the same manner as in Example 1, except that adenosine was used instead of 2-Cl-C.OXT-A and the final concentrations of the adenosine in the lumen formation media were set to 100 µmol/l, 1, 2.5, and 5 mmol/l.

Comparative Example 6

In the present example, the effect of deoxyadenosine on the lumen formation by vascular endothelial cells was examined.

The lumen formation was measured in the same manner as in Example 1, except that deoxyadenosine was used instead of 2-Cl-C.OXT-A and the final concentrations of the deoxyadenosine in the lumen formation media were set to 100, 500 µmol/l, 1, and 2.5 mmol/l.

Comparative Example 7

In the present example, the effect on the cell proliferation, lumen formation, and cell migration of vascular endothelial cells was examined in the same manner as in Example 1, except that VEGF was used as a positive control instead of 2-Cl-C.OXT-A and the final concentrations of VEGF in the cell proliferation medium, the lumen formation medium, and the migration measurement medium were set to 10 ng/ml.

Comparative Example 8

In the present example, the effect on the cell proliferation, lumen formation, and cell migration of vascular endothelial cells was examined in the same manner as in Example 1, except that, instead of the sample solutions, physiological saline was added to the cell proliferation medium, the lumen formation medium, and the migration measurement medium.

Comparative Example 9

In the present example, the effect on the cell migration of vascular endothelial cells was examined in the same manner as in Example 1, except that, instead of the sample solutions, fetal bovine serum (FBS) was added to the migration measurement medium and the final concentration of FBS in the medium was set to 5 v/v %.

Comparative Example 10

In the present example, the effect on the cell migration of vascular endothelial cells was examined in the same manner as in Example 1, except that, instead of the sample solutions, fetal bovine serum (FBS) was added to the migration measurement medium and the final concentration of the FBS in the medium was set to 10 v/v %.

<Results of Cell Proliferation Measurement>

Figure 2:
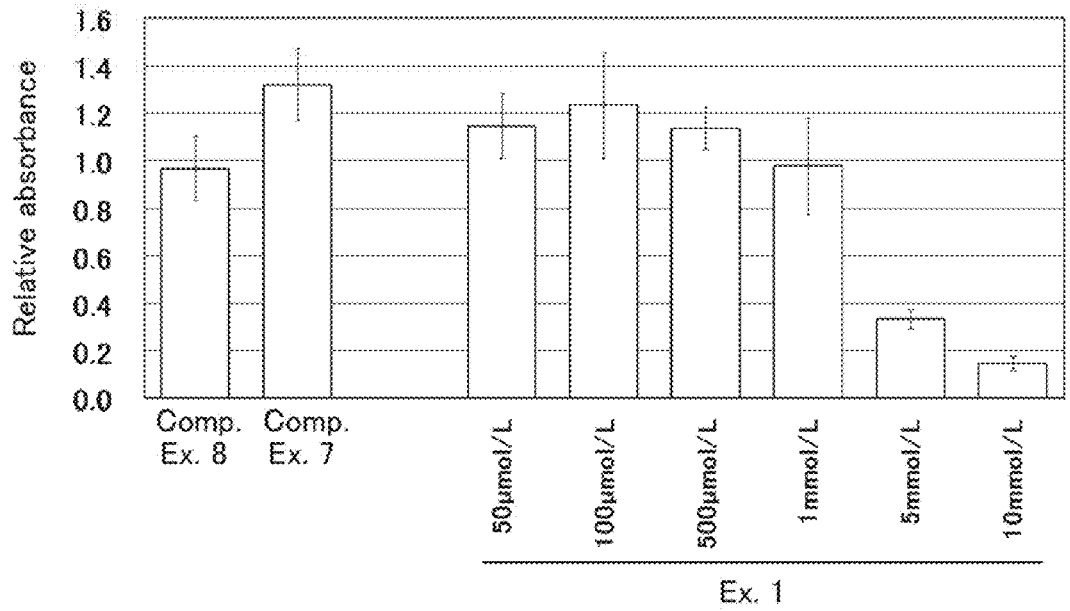
FIG. 2 is a graph showing the results of the cell proliferation measurement in Example 1 and Comparative Examples 7 and 8.

FIG. 2 is a graph comparing the relative absorbances obtained in the measurement of the cell proliferation. In the graph of FIG. 2, the vertical axis indicates the relative absorbance, and the respective bars indicate, from the left, the results obtained in Comparative Example 8 (physiological saline), Comparative Example 7 (VEGF), and Example 1 (2-Cl-C.OXT-A). The concentrations shown under the horizontal axis are the final concentrations of the samples in the cell proliferation media in Example 1.

As can be seen from the graph of FIG. 2, in Example 1, when the final concentration of 2-Cl-C.OXT-A was in the range from 50 µmol/l to 1 mmol/l, the relative absorbance was mostly higher than 1 and the proliferation was promoted slightly by 2-Cl-C.OXT-A, and when the final concentration was in a high concentration range of 5 mmol/l or higher, the proliferation was suppressed in a concentration-dependent manner.

<Results of Lumen Formation Measurement>

Figure 3A:
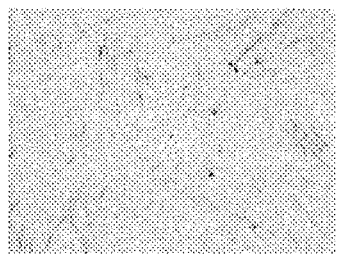
FIGS. 3A to 3F are photographs showing the results of the lumen formation measurement in Example 1 and Comparative Examples 7 and 8.
Figure 3B:
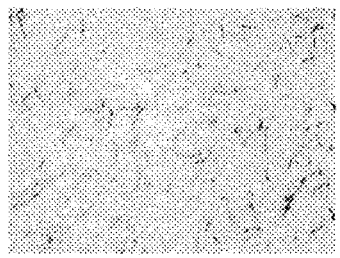
Figure 3C:
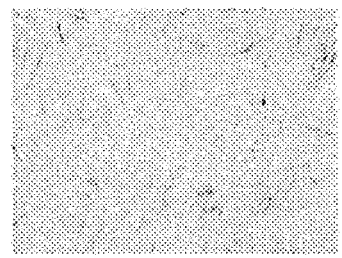
Figure 3D:
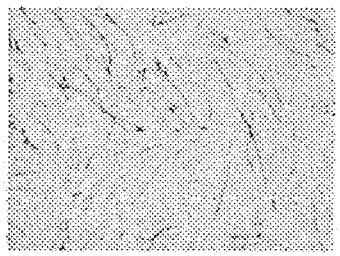
Figure 3E:
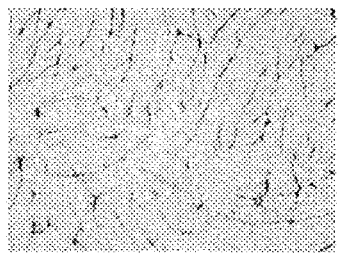
Figure 3F:
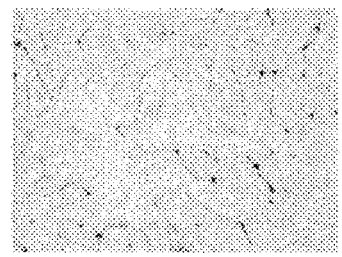

FIGS. 3A to 3F are photographs showing the results of the immunostaining in the measurement of lumen formation. FIG. 3A is a photograph showing the result obtained in Comparative Example 8 (physiological saline), FIG. 3B is a photograph showing the result obtained in Comparative Example 7 (VEGF), FIG. 3C is a photograph showing the result obtained in Example 1 (2-Cl-C.OXT-A, 1 µmol/l), FIG. 3D is a photograph showing the result obtained in Example 1 (2-Cl-C.OXT-A, 10 µmol/l), FIG. 3E is a photograph showing the result obtained in Example 1 (2-Cl-C.OXT-A, 100 µmol/l), and FIG. 3F is a photograph showing the result obtained in Example 1 (2-Cl-C.OXT-A, 1 mmol/l). In FIG. 3, the horizontal width of each photograph is 6 mm. In each photograph of FIG. 3, black linear objects are the immunostained human umbilical vein endothelial cells (HUVEC), and the greater the area of the black portions becomes, the more strongly the lumen formation was promoted.

As can be seen from the photographs of FIGS. 3D to 3F, when the final concentration of 2-Cl-C.OXT-A in the lumen formation medium was in the range from 10 µmol/l to 1 mmol/l, the stained area was larger than that in the control, so that the lumen formation promoting-activity of 2-Cl-C.OXT-A was confirmed. Furthermore, as can be seen from FIGS. 3D and 3E, when the final concentrations of 2-Cl-C.OXT-A were 10 and 100 µmol/l, the exhibited lumen formation promoting-activities were higher than that in Comparative Example 7 in which VEGF was added.

FIG. 1 is a graph comparing the relative values of lumen area. In the graph of FIG. 1, the vertical axis indicate the relative value of lumen area, and the respective bars indicate, from the left, the results obtained in Comparative Example 8 (physiological saline), Comparative Example 7 (VEGF), Example 1 (2-Cl-C.OXT-A), Comparative Example 1 (C.OXT-A), Comparative Example 2 (C.OXT-G), Comparative Example 3 (2-Cl-ADN), Comparative Example 4 (2-Cl-DAD), Comparative Example 5 (adenosine), and Comparative Example 6 (deoxyadenosine). The concentrations shown under the horizontal axis are the final concentrations of the samples in the lumen formation media in the respective examples.

As can be seen from the graph of FIG. 1, when the final concentration of 2-Cl-C.OXT-A was in the range from 100 nmol/l to 1 mmol/l, the relative values of lumen area were larger than that of the control, so that the lumen formation promoting-activity of 2-Cl-C.OXT-A was confirmed. When the final concentration was in the range from 10 to 500 µmol/l, the exhibited lumen formation promoting-activities were higher than that in Comparative Example 7 in which VEGF was added. In particular, when the final concentration was 100 µmol/l, the relative value of lumen area was 3.8 and the highest lumen formation promoting-activity was exhibited.

<Result of Cell Migration Measurement>

Figure 4A:
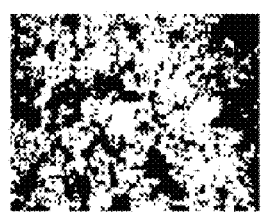
FIGS. 4A to 4H are photographs showing the results of the cell migration measurement in Example 1 and Comparative Examples 7 to 10.
Figure 4B:
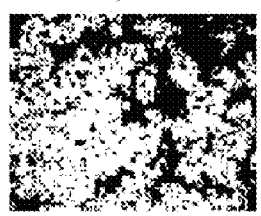
Figure 4C:
Figure 4D:
Figure 4E:
Figure 4F:
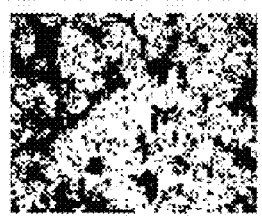
Figure 4G:
Figure 4H:

FIGS. 4A to 4H and FIGS. 5A to 5H show photographs showing the results of the staining in the measurement of cell migration. FIGS. 4A and 5A are photographs showing the results obtained in the control, FIGS. 4B and 5B are photographs showing the results obtained in Comparative Example 8 (physiological saline), FIGS. 4C and 5C are photographs showing the results obtained in Comparative Example 9 (5 v/v % FBS), FIGS. 4D and 5D are photographs showing the results obtained in Comparative Example 10 (10 v/v % FBS), FIGS. 4E and 5E are photographs showing the results obtained in Comparative Example 7 (VEGF), FIGS. 4F and 5F are photographs showing the results obtained in Example 1 (2-Cl-C.OXT-A, 10 µmol/l), FIGS. 4G and 5G are photographs showing the results obtained in Example 1 (2-Cl-C.OXT-A, 50 µmol/l), and FIGS. 4H and 5H are photographs showing the results obtained in Example 1 (2-Cl-C.OXT-A, 100 µmol/l). In both FIGS. 4 and 5, the horizontal width of each photograph is 1.6 mm. In each of the photographs of FIGS. 4 and 5, portions stained black indicate the human umbilical vein endothelial cells (HUVEC) that had migrated.

The greater the area of the black portions becomes, the more strongly the cell migration was promoted.

As can be seen from the photographs of FIGS. 4F to 4H and FIGS. 5F to 5H, when the final concentration of 2-Cl-C.OXT-A in the culture solution was in the range from 10 µmol/l to 100 µmol/l, the stained areas were larger than that in the control, so that the cell migration promoting-activity of 2-Cl-C.OXT-A was confirmed.

FIG. 6 is a graph comparing the relative absorbances obtained in the measurement of cell migration. In the graph of FIG. 6, the vertical axis indicates the relative absorbance, and the respective bars indicate, from the left, the results obtained in the control (cell migration medium), Comparative Example 8 (physiological saline), Comparative Example 9 (5 v/v % FBS), Comparative Example 10 (10 v/v % FBS), Comparative Example 7 (VEGF), and Example 1 (2-Cl-C.OXT-A). Regarding the bars indicating the results obtained in Example 1, the concentrations shown under the horizontal axis are the final concentrations of 2-Cl-C.OXT-A in the cell migration media.

As can be seen from the graph of FIG. 6, when the final concentration of 2-Cl-C.OXT-A was in the range from 10 to 100 µmol/l, the relative absorbances were higher than that of the control, so that the cell migration promoting-activity by 2-Cl-C.OXT-A was confirmed. When the final concentrations were 50 and 100 µmol/l, the exhibited migration promoting-activities were significantly higher than that in Comparative Example 8 in which physiological saline was added (p<0.02). In particular, when the final concentration was 50 µmol/l, the relative absorbance was 2.1, and the exhibited cell migration promoting-activity was higher than that in Comparative Example 7 in which VEGF was added.

Example 2

In the present example, 6-amino-2-thiomethoxy-9-[trans-trans-2,3-bis (hydroxymethyl)cyclobutyl]purine ($C_{12}H_{17}N_5O_2S$, hereinafter referred to as "2-SMe-C.OXT-A") represented by the above chemical formula (9) was synthesized. In the chemical formula (9), MeS denotes a methylthio group.

<Synthesis of 2-SMe-C.Oxt-A>

In the present example, 6-amino-2-chloro-9-[trans-trans-2,3-bis (hydroxymethyl)cyclobutyl]purine (2-Cl-C.OXT-A) was synthesized by carrying out the steps 1 to 3 in the same manner as in Example 1. Then, using the thus-obtained 2-Cl-C.OXT-A, the following steps 4 to 6 further were carried out. Thus, 2-SMe-C.OXT-A was synthesized. In the present example, each compound was measured in the same manner as in Example 1.

(Step 4: Synthesis of 6-amino-2-chloro-9-[trans-trans-2,3-bis (triphenylmethoxymethyl)cyclobutyl]purine)

The 6-amino-2-chloro-9-[trans-trans-2,3-bis(hydroxymethyl)cyclobutyl]purine (170.4 mg, 0.60 mmol) solution, trityl chloride (501.8 mg, 1.80 mmol), triethylamine (0.4 ml), and 4-dimethylaminopyridine (11.6 mg, 0.06 mmol) were dissolved in 2.0 ml of DMF and stirred at room temperature overnight. 12 hours after the start of the stirring, the cloudy yellow liquid obtained was added to ice water and subjected to extraction using ethyl acetate. This organic extract was washed with a saturated ammonium chloride solution and water, and then dried using sodium sulfate. The solvent was evaporated, and thereafter, the residual substance was purified by silica gel column chromatography. Thus, white crystals of 6-amino-2-chloro-9-[trans-trans-2,3-bis(triphenylmethoxymethyl)cyclobutyl]purine represented by the following chemical formula (15) (273.9 mg, yield: 59%) were obtained. In the following chemical formula (15), Tr denotes a trityl group.

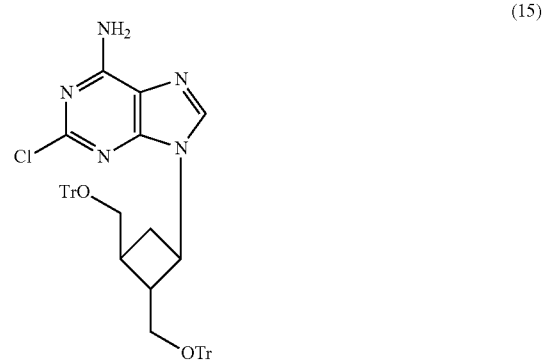

(15)

Physical properties of this compound are shown below.
$^1$H NMR (400 MHz, CDCl$_3$): δ 7.91 (1H, s), 7.15-7.41 (30H, m), 5.70 (2H, br s), 4.73 (1H, dd, J 17.2 and 9.2), 3.70 (1H, dd, J 10.0 and 4.8), 3.18-3.30 (4H, m), 2.87-2.90 (1H, m), 2.53-2.67 (1H, m), 2.20-2.33 (2H, m).

(Step 5: Synthesis of 6-amino-2-thiomethoxy-9-[trans-trans-2,3-bis (triphenyl methoxymethyl)cyclobutyl]purine)

The 6-amino-2-chloro-9-[trans-trans-2,3-bis(triphenylmethoxymethyl)cyclobutyl]purine (92.2 mg, 0.12 mmol) and sodium thiomethoxide (84.1 mg, 1.20 mmol) were dissolved in 3.1 ml of DMF, and the resultant solution was heated at 110° C. for 3.5 hours. After the completion of the heating, the solvent was evaporated under reduced pressure, and the residual substance obtained was subjected to extraction using ethyl acetate. The organic extract obtained was washed with water and a saturated sodium chloride solution, and then dried using sodium sulfate. Thereafter, the solvent was evaporated under reduced pressure. The residual substance obtained was purified by silica gel column chromatography (ethyl acetate: hexane=1:1). Thus, yellowish crystals of 6-amino-2-thiomethoxy-9-[trans-trans-2,3-bis (triphenylmethoxymethyl)cyclobutyl]purine represented by the following chemical formula (16) (66.3 mg, yield: 71%) were obtained. In the following chemical formula (16), MeS denotes a methylthio group, and Tr denotes a trityl group.

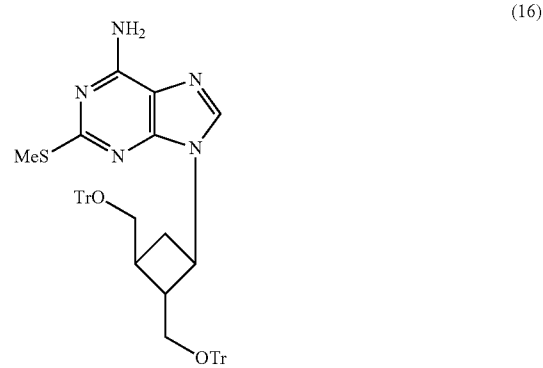

(16)

Physical properties of this compound are shown below.
$^1$H NMR (400 MHz, CDCl$_3$): δ 7.68 (1H, s), 7.14-7.41 (30H, m), 5.43 (2H, br s), 4.74 (1H, dd, J 17.6 and 8.8), 3.18-3.33 (4H, m), 2.90-3.03 (1H, m), 2.53-2.65 (1H, m), 2.33-2.48 (2H, m), 2.29 (3H, s).

(Step 6: Synthesis of 2-SMe-C.Oxt-A)

The 6-amino-2-thiomethoxy-9-[trans-trans-2,3-bis (triphenylmethoxymethyl)cyclobutyl]purine (65.0 mg, 0.08 mmol) was dissolved in a mixture of 1.7 ml of formic acid and 1.7 ml of diethyl ether, and stirred at room temperature for 15 minutes. After the completion of the stirring, this mixture was dissolved in ethyl acetate to carry out extraction. The organic extract obtained was washed with a saturated sodium hydrogencarbonate solution and a saturated sodium chloride solution, and dried using sodium sulfate. The organic solvent was evaporated, and thereafter, the residual substance was purified by thin layer chromatography (dichloromethane:ethanol=5:1). Thus, yellowish crystals of 2-SMe-C.OXT-A (6-amino-2-thiomethoxy-9-[trans-trans-2,3-bis (hydroxymethyl)cyclobutyl]purine) represented by the chemical formula (9) (9.4 mg, yield: 38%) were obtained. Physical properties of this compound are shown below.

$^1$H NMR (400 MHz, MeOH-d$_4$): δ 8.04 (1H, s), 4.64 (1H, dd. J 17.6 and 8.8), 3.62-3.87 (4H, m), 2.85-3.00 (1H, m), 2.54 (1H, s), 2.42-2.61 (2H, m), 2.18-2.24 (1H, m); $^{13}$C NMR (100 MHz, MeOH-d$_4$): δ 167.5, 165.5, 155.2, 138.9, 118.2, 64.1, 62.2, 48.6, 33.5, 29.3, 28.2, 13.1. Mp 209.4° C. to 211.0° C. HRMS (ESI) Calcd for C$_{12}$H$_{17}$N$_5$NaO$_2$S [M+Na]$^+$: 318.0995. Found 318.1052.

The effect of 2-SMe-C.OXT-A of the present example on the cell proliferation, lumen formation, and cell migration of vascular endothelial cells was examined in the same manner as in Example 1. As a result, 2-SMe-C.OXT-A exhibited cell proliferation promoting-activity, lumen formation promoting-activity, and cell migration promoting-activity for vascular endothelial cells.

Example 3

In the present example, the effect of 2-Cl-C.OXT-A used in Example 1 on the activation (phosphorylation) of enzymes, namely, ERK, Akt, JNK, and p38, was examined. These proteins are specifically as follows: ERK is one of the most typical angiogenesis promoting protein kinases in endothelial cells; Akt also is one of the most typical angiogenesis promoting protein kinases in endothelial cells, along with the ERK pathway; and JNK and p38 are typical protein kinases of the MAP kinase family, which form pathways different from the ERK pathway.

First, to a HuMedia-EB2 medium (Kurabo) to which 2 v/v % inactivated fetal bovine serum (FBS) had been added, 2-Cl-C.OXT-A was added so that its concentration became 100 μmol/l. Thus, a medium was prepared. Using the medium, human umbilical vein endothelial cells (HUVEC) were cultured for predetermined periods (0, 10, 20, 30, 45, and 60 minutes).

After the culture, cells were collected. The collected cells were lysed by adding a cell lysis buffer (SDS-lysis buffer) thereto, and heat-denatured at 95° C. for 5 minutes. The solubilized protein in an amount corresponding to 5 v/v % of the heat-denatured cell lysate was subjected to electrophoresis using 10% SDS-polyacrylamide gel, whereby the solubilized protein was transferred onto a nitrocellulose membrane (Amersham Biosciences). To 20 ml of TBS-T having the following composition, skim milk (Wako) was added so that its concentration became 5%, thus preparing a blocking solution. The resultant nitrocellulose membrane was immersed in the blocking solution and shaken at room temperature for 1 hour.

(Composition of TBS-T)
10 mmol/l Tris
0.15 mol/l NaCl
0.1% Tween (registered trademark)-20

Primary antibodies shown below were diluted 1000-fold by adding them to 5% bovine serum albumin (Sigma)-containing TBS-T, thus preparing a primary antibody solution. The nitrocellulose membrane after being subjected to the blocking was immersed in the primary antibody solution, and shaken at room temperature for 1 hour. The resultant nitrocellulose membrane was immersed in the TBS-T and washed by being shaken for 10 minutes. This washing operation was carried out three times in total.

(Primary Antibody)
anti-phospho ERK polyclonal antibody (Catalog No. 9101, Cell Signaling Technology)
anti-phospho Akt polyclonal antibody (Catalog No. 9271, Cell Signaling Technology)
anti-phospho p38 polyclonal antibody (Catalog No. 9211, Cell Signaling Technology)
anti-phospho JNK polyclonal antibody (Catalog No. 9251, Cell Signaling Technology)
anti-total ERK monoclonal antibody (Catalog No. 610408, BD Transduction Laboratory)
anti-total Akt polyclonal antibody (Catalog No. 9272, Cell Signaling Technology)

Secondary antibodies shown below were diluted 20000-fold by adding them to TBS-T, thus preparing a secondary antibody solution. The nitrocellulose membrane having undergone the reaction with the primary antibodies was immersed in the secondary antibody solution, and shaken at room temperature for 1 hour. The resultant nitrocellulose membrane was immersed in the TBS-T and washed by being shaken for 10 minutes. This washing operation was carried out three times in total.

(Secondary Antibody)
ERK:
sheep HRP-labeled anti-mouse IgG antibody (Pierce)
pERK, Akt, pAkt, pJNK, and pp 38:
sheep HRP-labeled anti-rabbit IgG antibody (Pierce)

The enzymes were visualized with SuperSignal (registered trademark) West Pico Chemiluminescent Substrate (Pierce), and detected by being exposed to RX—U X-ray film (FUJIFILM Corporation). From the detected bands, the respective phosphoenzymes and total enzymes were quantified using an NIH image software. Furthermore, the relative value (−fold) of each phosphoenzyme was calculated by substituting the measured value of the phosphoenzyme into the following equation (III).

$$\text{Relative value (−fold) of phosphoenzyme} = (B/D)/(A/C) \qquad \text{(III)}$$

A=measured value of each phosphoenzyme before adding 2-Cl-C.OXT-A

Figure 7A:
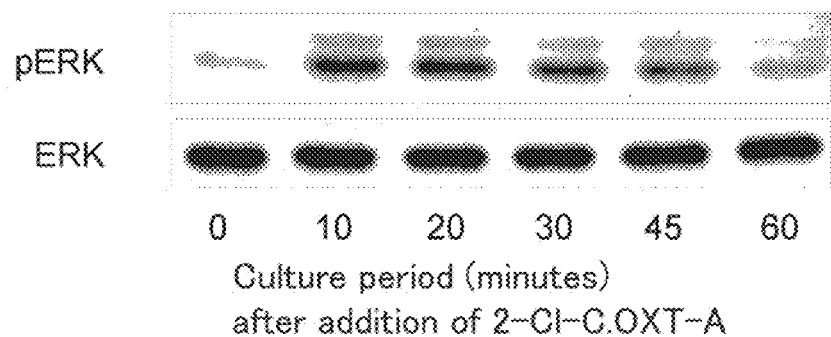
FIG. 7A shows immunoblot photographs showing the amounts of pERK and ERK over time in Example 3.
Figure 7B:
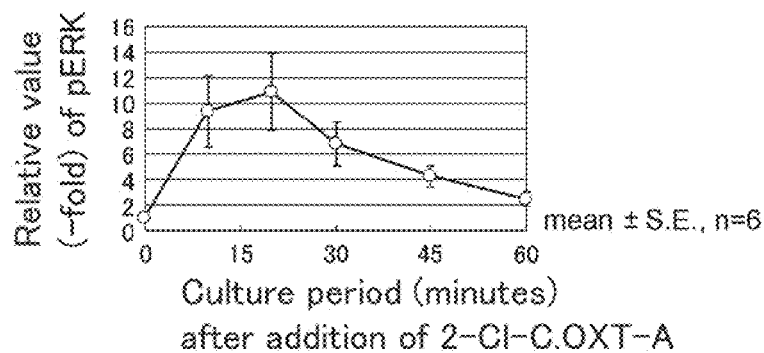
FIG. 7B is a graph showing the relative value of pERK.
Figure 8:
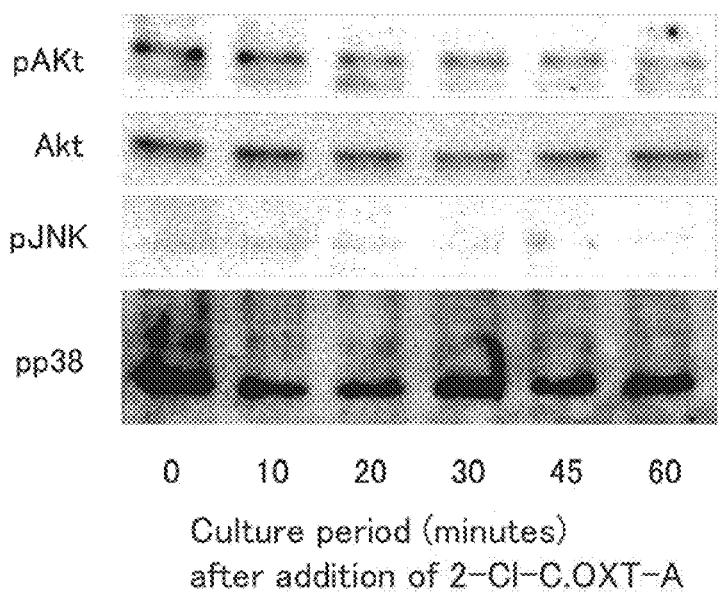
FIG. 8 shows immunoblot photographs showing the amounts of pAkt, Akt, pJNK, and pp38 over time in Example 3.

B=measured value of each phosphoenzyme after a lapse of respective times from the addition of 2-Cl-C.OXT-A C=measured value of each total enzyme before adding 2-Cl-C.OXT-A D=measured value of each total enzyme after a lapse of respective times from the addition of 2-Cl-C.OXT-A FIGS. 7 and 8 show the results of measuring the amounts of the phosphoenzymes in ERK, Akt, JNK, and p38 over time. FIG. 7A shows immunoblot photographs regarding, from the top, phosphorylated ERK (pERK) and ERK, and the results shown in these photographs are, from the left, those obtained 0, 10, 20, 30, 45, and 60 minutes after the addition of 2-Cl-C.OXT-A. FIG. 7B is a graph showing the results of quantification of pERK shown in FIG. 7A. In FIG. 7B, the horizontal axis indicates the culture period (minutes) after the addition of 2-Cl-C.OXT-A, and the vertical axis indicates the relative value (-fold) of pERK. FIG. 8 shows immunoblot photographs regarding, from the top, phosphorylated Akt (pAkt), Akt, phosphorylated JNK (pJNK), and phosphorylated p38 (pp 38), and the results shown in these photographs are, from the left, those obtained 0, 10, 20, 30, 45, and 60 minutes after the addition of 2-Cl-C.OXT-A.

As can be seen from FIG. 7, pERK increased in proportion to the culture period, and 20 minutes after the addition of 2-Cl-C.OXT-A, pERK increased about 11-fold. In contrast, as can be seen from FIG. 8, the amounts of pAkt, pJNK, and pp 38 were not changed by the addition of 2-Cl-C.OXT-A. As is clear from these results, the activation (phosphorylation) of ERK as a signal transducer involved in angiogenesis was promoted by 2-Cl-C.OXT-A.

Example 4

In the present example, the effect of 2-Cl-C.OXT-A of Example 1 and C.OXT-G of Comparative Example 2 on the activation (phosphorylation) of ERK was examined. In the present example, the amount of each enzyme was measured and the relative value (-fold) of each phosphoenzyme was calculated in the same manner as in Example 3, except that: a medium to which 2-Cl-C.OXT-A had been added so as to achieve predetermined concentrations (0, 10 and 100 μmol/l) and a medium to which 100 μmol/l C.OXT-G had been added were used; the culture period after the addition was set to 20 minutes: as the primary antibodies, only an anti-phospho ERK polyclonal antibody (Catalog No. 9101, Cell Signaling Technology) and an anti-total ERK monoclonal antibody (Catalog No. 610408, BD Transduction Laboratory) were used; as the secondary antibody for ERK, a sheep HRP-labeled anti-mouse IgG antibody (Pierce) was used; and as a secondary antibody of pERK, a sheep HRP-labeled anti-rabbit IgG antibody (Pierce) was used.

Figure 9A:
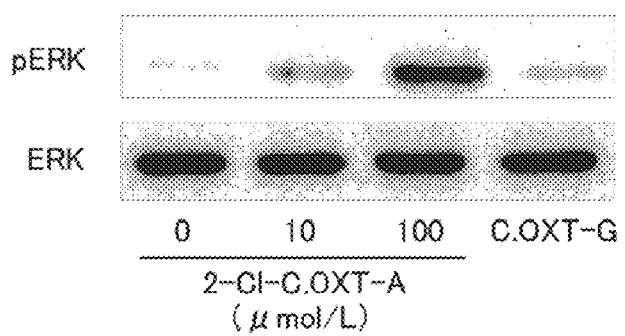
FIG. 9A shows immunoblot photographs showing the influence of the concentration of the added 2-Cl—OCT-A on the amount of pERK in Example 4 of the present invention.
Figure 9B:
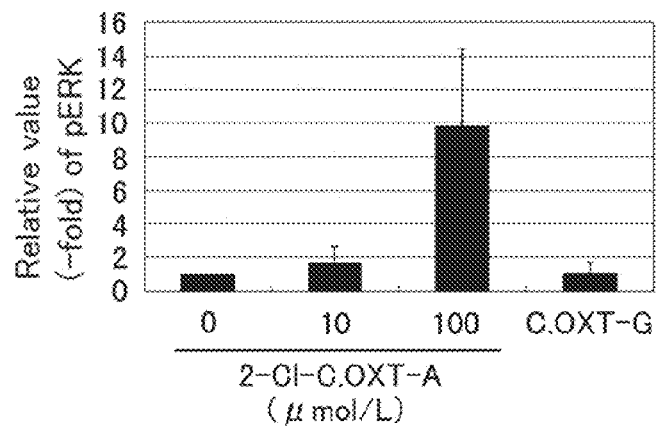
FIG. 9B is a graph showing the relative value of pERK.

FIG. 9 shows the results of measuring the phosphorylated ERK at the respective concentrations of the added substance. In FIG. 9A, the upper row is an immunoblot photograph regarding the phosphorylated ERK (pERK), the lower row is an immunoblot photograph regarding ERK, and the results shown in these photographs are, from the left, those obtained when 2-Cl-C.OXT-A was added at concentrations of 0, 10 and 100 μmol/l and when C.OCT-G was added. FIG. 9B is a graph, showing the results of quantification of pERK in FIG. 9A. In FIG. 9B, the vertical axis indicates the relative value (-fold) of pERK, and the respective bars indicate, from the left, the results obtained when 2-Cl-C.OXT-A was added at concentrations of 0, 10 and 100 μmol/l and when C.OCT-G was added.

As can be seen from FIG. 9, pERK increased in a manner dependent on the concentration of the added 2-Cl-C.OXT-A, and when the concentration of 2-Cl-C.OXT-A was 100 μmol/l, pERK increased about 10-fold. In contrast, the amount of pERK was not increased by the addition of C.OCT-G. As is clear from these results, by adding 2-Cl-C.OXT-A so that its concentration became 10 μmol/l or 100 μmol/l, ERK as a signal transducer involved in angiogenesis was activated.

Example 5

In the present example, the effect of 2-Cl-C.OXT-A used in Example 1 on the phosphorylation of MEK was examined. MEK is a protein kinase involved in the angiogenesis signal transduction pathway and located upstream of ERK measured in Example 3, and acts to promote angiogenesis. In the present example, the amount of each enzyme was measured and the relative value (-fold) of each phosphoenzyme was calculated in the same manner as in Example 3, except that: the culture period after the addition of 2-Cl-C.OXT-A was set to predetermined periods (0, 5, 10, 15, and 20 minutes); as the primary antibodies, an anti-phospho MEK polyclonal antibody (Catalog No. 9121, CellSignaling Technology) and an anti-total MEK polyclonal antibody (Catalog No. 9122, Cell Signaling Technology) were used; and as the secondary antibody, a sheep HRP-labeled anti-rabbit IgG antibody (Pierce) was used.

Figure 10A:
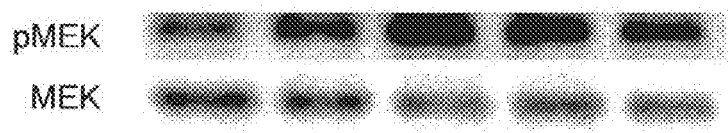
FIG. 10A shows immunoblot photographs showing the amounts of pMEK and MEK over time in Example 5, and FIG. 10B a graph showing the relative value of pMEK.
Figure 10B:
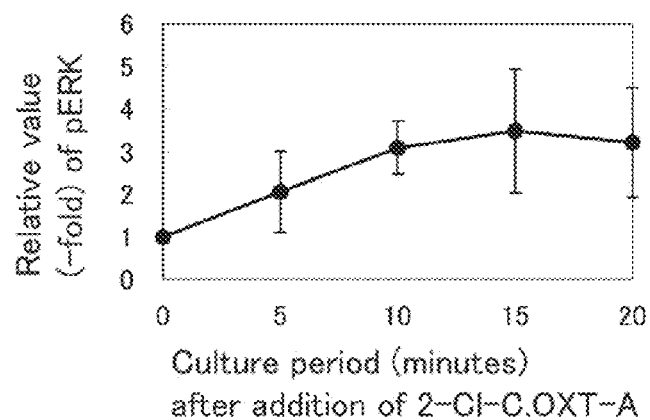

In FIG. 10A, the upper row is an immunoblot photograph regarding pMEK (phosphorylated MEK), the lower row is an immunoblot photograph regarding MEK, and the results shown in these photographs are, from the left, those obtained 0, 5, 10, 15 and 20 minutes after the addition of 2-Cl-C.OXT-A. FIG. 10B is a graph showing the results of quantification of pMEK shown in FIG. 10A. In FIG. 10B, the horizontal axis indicates the culture period (minutes) after the addition of 2-Cl-C.OXT-A, and the vertical axis indicates the relative value (-fold) of pMEK. As can be seen from FIG. 10, pMEK increased in proportion to the culture period, and 15 minutes after the addition of 2-Cl-C.OXT-A, it increased about 3.5-fold. As is clear from these results, the activation (phosphorylation) of MEK as a signal transducer involved in angiogenesis was promoted by 2-Cl-C.OXT-A.

Example 6

In the present example, the effect of PD98059 as an MEK inhibitor on the ERK activation (phosphorylation) by 2-Cl-C.OXT-A used in Example 1 was examined. In the present example, the amount of each enzyme was measured and the relative value (-fold) of each phosphoenzyme was calculated in the same manner as in Example 4, except that media Nos. 1 to 4 prepared by adding, to HuMedia-EB2 media (Kurabo) to which 2 v/v % inactivated fetal bovine serum (FBS) had been added, 2-Cl-C.OXT-A and PD98059 so that their concentrations became as shown in Table 1 below were used.

TABLE 1

| Medium No. | 2-Cl—C•OXT-A (μmol/l) | PD98059 (nmol/l) |
|---|---|---|
| 1 | 0 | 0 |
| 2 | 100 | 0 |
| 3 | 0 | 100 |
| 4 | 100 | 100 |

Figure 11A:
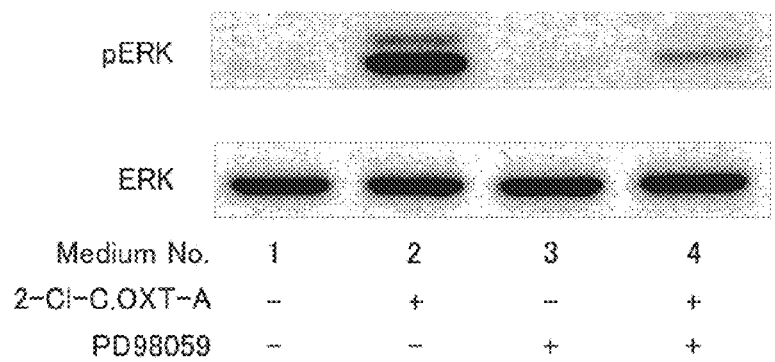
FIG. 11A shows immunoblot photographs showing the inhibition of ERK activation by PD98059 in Example 6.
Figure 11B:
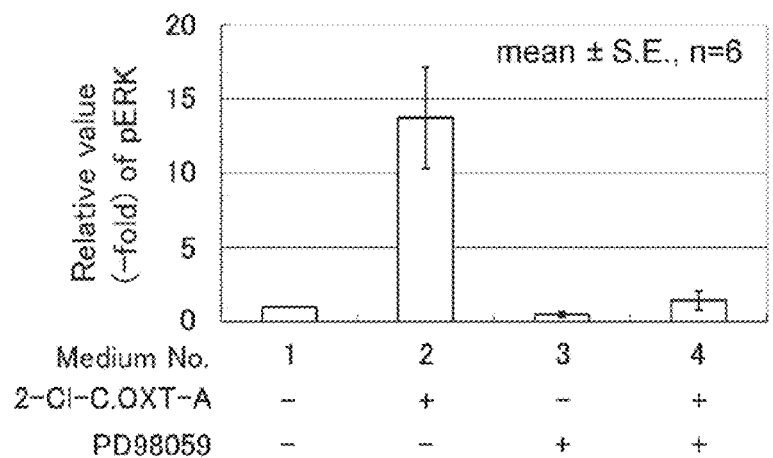
FIG. 11B is a graph showing the relative value of pERK.

FIG. 11 shows the results of measuring the ERK activation (phosphorylation) inhibitory effect by PD98059. In FIG. 11A, the upper row is an immunoblot photograph regarding pERK (phosphorylated ERR), the lower row is an immunoblot photograph regarding ERK as a whole, and the results shown in these photographs are, from the left, those obtained when the media No. 1, No. 2, No. 3, and No. 4 were used. FIG. 11B is a graph showing the results of quantification of pERK shown in FIG. 11A. In FIG. 11B, the vertical axis indicates the relative value (-fold) of pERK (pERK1 and pERK2), and the respective bars indicate, from the left, the results obtained when the media No. 1, No. 2, No. 3, and No. 4 were used.

As can be seen from FIG. 11, pERK increased in the medium No. 2 to which 2-Cl-C.OXT-A had been added. However, in the medium No. 4 in which PD98059 was present together with 2-Cl-C.OXT-A, increase in pERK was not observed. Furthermore, in the medium No. 1 containing no 2-Cl-C.OXT-A and the medium No. 3 to which only PD98059 had been added, increase in pERK also was not observed. As is clear from these results, the ERK activation by 2-Cl-C.OXT-A was inhibited by PD98059. This suggests that the ERK activation by 2-Cl-C.OXT-A is caused via a specific MAP kinase pathway mediated by MEK.

Example 7

In the present example, the effect of PD98059 as a MEK inhibitor on the lumen formation by 2-Cl-C.OXT-A used in Example 1 was examined.

In the present example, the relative value of lumen area was calculated in the same manner as in the lumen formation measurement in Example 1, except that the measurement was carried out with respect to four groups respectively using media Nos. 5 to 8 prepared by adding 2-Cl-C.OXT-A and PD98059 to media provided in the above-described angiogenesis kits (Kurabo) so that their concentrations became as shown in Table 2 below. In the group using the medium No. 7, the culture was conducted using the medium No. 7 from the first to third days of the culture and the medium No. 5 from the fourth to tenth days of the culture, and in the group using the medium No. 8, the culture was conducted using the medium No. 8 from the first to third days of the culture and the medium No. 6 from the fourth to tenth days of the culture.

TABLE 2

| Medium No. | 2-Cl—C•OXT-A (μmol/l) | PD98059 (nmol/l) |
| --- | --- | --- |
| 5 (control) | 0 | 0 |
| 6 | 10 | 0 |
| 7 | 0 | 10 |
| 8 | 10 | 10 |

Figure 12:
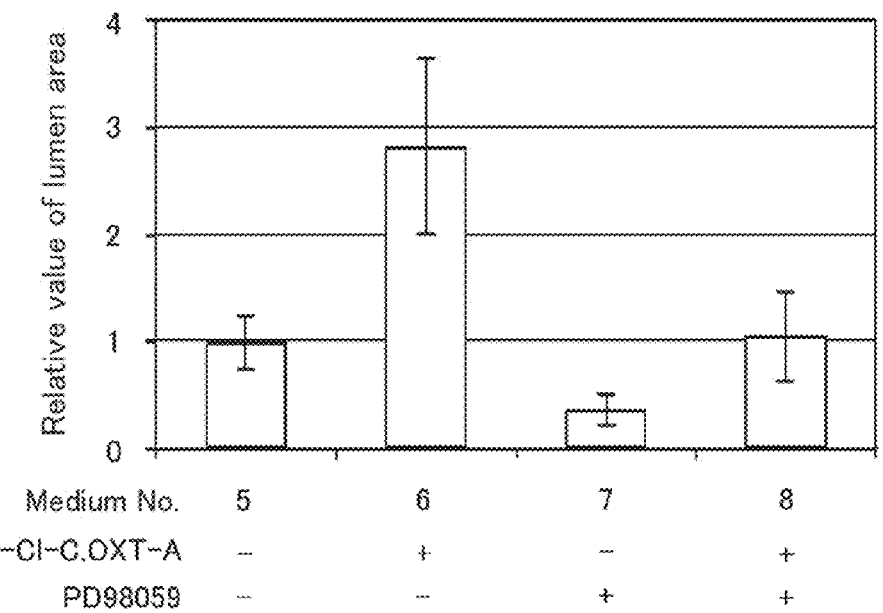
FIG. 12 is a graph showing the relative value of lumen area that indicates the inhibition of lumen formation by PD98059 in Example 7 of the present invention.

FIG. 12 is a graph comparing the relative values of lumen area. In FIG. 12, the vertical axis indicates the relative value of lumen area, and the respective bars indicate, from the left, the measurement results obtained in the groups using the media No. 5, No. 6, No. 7, and No. 8, respectively. In the group using the medium No. 6 to which only 2-Cl-C.OXT-A had been added, the relative value of lumen area was about 3-fold as compared with that of the group using the medium No. 5 (control). However, by using the PD98059 in combination, the increase was suppressed to about 1-fold. These results demonstrate that the lumen formation promotion by 2-Cl-C.OXT-A is inhibited by PD98059, similarly to the ERK activation described above.

Example 8

In the present example, the effect of SU5416 as a VEGFR inhibitor on the ERK activation (phosphorylation) by 2-Cl-C.OXT-A used in Example 1 was examined. In the present example, the amount of each enzyme was measured and the relative value (–fold) of each phosphoenzyme was calculated in the same manner as in Example 4, except that media Nos. 9 to 14 prepared by adding, to HuMedia-EB2 media (Kurabo) to which 2 v/v % inactivated fetal bovine serum (FBS) had been added, 2-Cl-C.OXT-A and SU5416 so that their concentrations became as shown in Table 3 below were used.

TABLE 3

| Medium No. | 2-Cl—C•OXT-A (μmol/l) | VEGF (ng/ml) | SU5416 (nmol/l) |
| --- | --- | --- | --- |
| 9 | 0 | 0 | 0 |
| 10 | 0 | 0 | 100 |
| 11 | 100 | 0 | 0 |
| 12 | 100 | 0 | 100 |
| 13 | 0 | 10 | 0 |
| 14 | 0 | 10 | 100 |

Figure 13A:
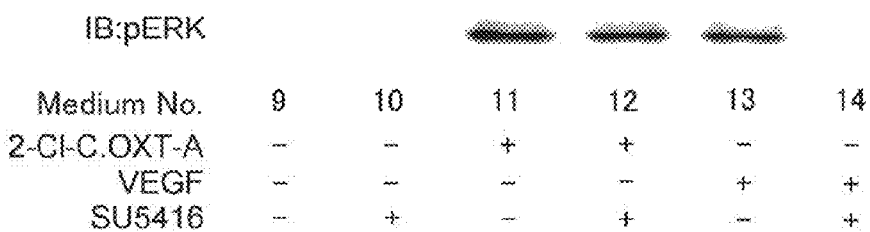
FIG. 13A shows immunoblot photographs showing the inhibition of ERK activation by SU5416 in Example 8.
Figure 13B:
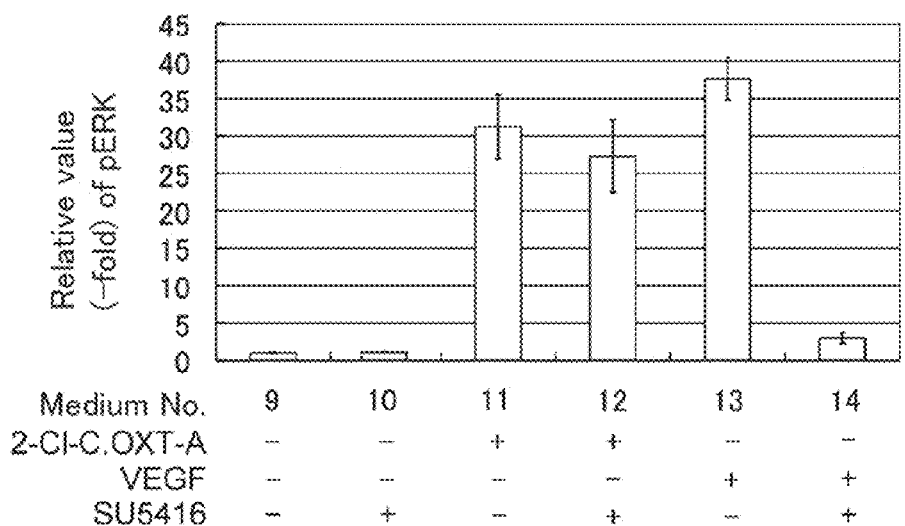
FIG. 13B is a graph showing the relative value of pERK.

FIG. 13 shows the results of measuring the ERK activation (phosphorylation) inhibitory effect by SU5416. FIG. 13A is an immunoblot photograph regarding pERK (phosphorylated ERK), and the results shown in this photograph are, from the left, those obtained when the media No. 9, No. 10, No. 11, No. 12, No. 13, and No. 14 were used. FIG. 13B is a graph showing the results of quantification of pERK (pERK1 and pERK2) shown in FIG. 13A. In FIG. 13B, the vertical axis indicates the relative value (–fold) of pERK (pERK1 and pERK2), and the respective bars indicate, from the left, the results obtained when the media No. 9, No. 10, No. 11, No. 12, No. 13, and No. 14 were used.

As can be seen from FIG. 13, pERK increased in the medium No. 11 to which 2-Cl-C.OXT-A had been added and also in the medium No. 12 in which SU5416 was present together with 2-Cl-C.OXT-A. In the medium No. 9 containing no 2-Cl-C.OXT-A and the medium No. 10 to which only SU5416 had been added, increase in pERK was not observed. On the other hand, pERK increased in the medium No. 13 to which VEGF as a positive control had been added, whereas the increase thereof was suppressed in the medium No. 14 in which SU5416 was present together with VEGF. As is clear from these results, the ERK activation by 2-Cl-C.OXT-A was not inhibited by SU5416. This demonstrates that, unlike VEGF as a positive control, the ERK activation mechanism by 2-Cl-C.OXT-A does not depend on the activity of a VEGF receptor.

Example 9

In the present example, the effect of SU5416 as a VEGFR inhibitor on the lumen formation by 2-Cl-C.OXT-A used in Example 1 was examined.

In the present example, the relative value of lumen area was calculated in the same manner as in the lumen formation measurement in Example 1, except that the measurement was carried out with respect to six groups respectively using media Nos. 15 to 20 prepared by adding 2-Cl-C.OXT-A, VEGF (positive control), and SU5416 to media provided in the above-described angiogenesis kit (Kurabo) so that their concentrations became as shown in Table 4 below. In the group using the medium No. 16, the culture was conducted using the medium No. 16 from the first to third days of the culture and the medium No. 15 from the fourth to tenth days of the culture; in the group using the medium No. 18, the culture was conducted using the medium No. 18 from the first to third days of the culture and the medium No. 17 from the fourth to tenth days of the culture; and in the group using the medium No. 20, the culture was conducted using the medium No. 20 from the first to third days of the culture and the medium No. 19 from the fourth to tenth days of the culture.

TABLE 4

| Medium No. | 2-Cl—C•OXT-A (μmol/l) | VEGF (ng/ml) | SU5416 (μmol/l) |
|---|---|---|---|
| 15(control) | 0 | 0 | 0 |
| 16 | 0 | 0 | 2.5 |
| 17 | 10 | 0 | 0 |
| 18 | 10 | 0 | 2.5 |
| 19 | 0 | 10 | 0 |
| 20 | 0 | 10 | 2.5 |

Figure 14:
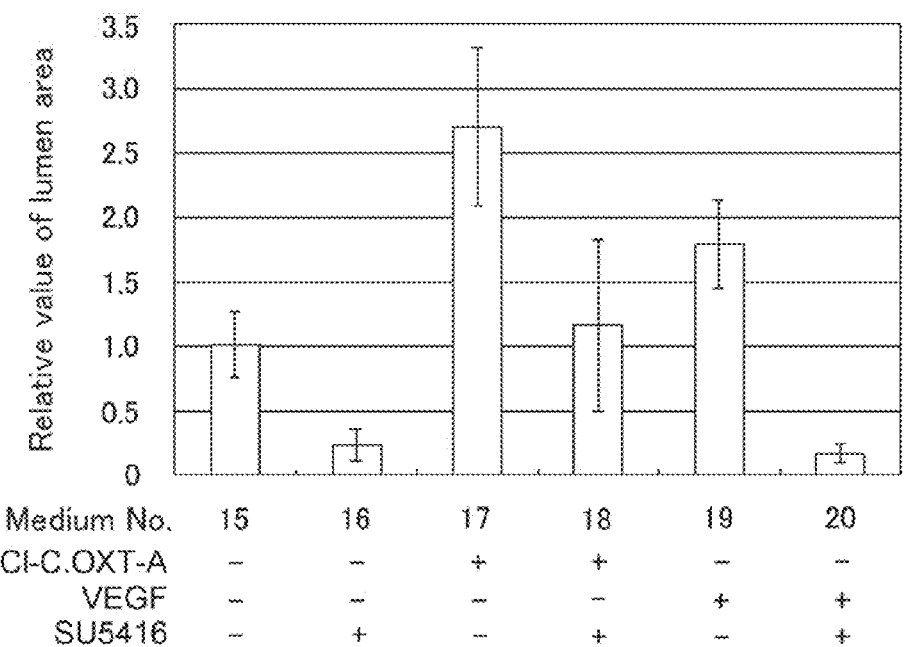
FIG. 14 is a graph showing the relative value of lumen area that indicates the inhibition of lumen formation by SU5416 in Example 9 of the present invention.

FIG. 14 is a graph comparing the relative values of lumen area. In FIG. 14, the vertical axis indicates the relative value of lumen area, and the respective bars indicate, from the left, the measurement results obtained in the groups using the media No. 15, No. 16, No. 17, No. 18, No. 19, and No. 20, respectively. As can be seen from FIG. 14, the lumen area increased in the medium No. 19 to which VEGF had been added, whereas it decreased in the medium No. 20 in which SU5416 was used in combination with VEGF. In contrast, in the medium No. 17 to which 2-Cl-C.OXT-A had been added, the lumen area increased markedly, and in the medium No. 18 in which SU5416 was used in combination with 2-Cl-C.OXT-A, the lumen area increased although the increase rate was lower that that when the medium No. 17 was used. As is clear from these results, the lumen formation promotion by 2-Cl-C.OXT-A was not inhibited by SU5416. The lumen formation in the medium No. 16 to which only SU5416 had been added decreased as compared with that in the medium No. 15 containing no SU5416 (control). The reason for this is considered to be that the lumen formation promotion by the fibroblast-derived VEGF used in this evaluation system was suppressed by adding SU5416. Therefore, it is speculated that the suppression of the increase in the medium No. 18 was caused by the fact that the lumen formation by the fibroblast-derived VEGF had been suppressed. Thus, it is demonstrated that the lumen formation promoting mechanism by 2-Cl-C.OXT-A does not depend on the activity of a VEGF receptor, similarly to the ERK activation promoting mechanism.

Example 10

In the present example, using rat adrenal medulla-derived cell line PC12, which is neurocyte model cells, obtained from the RIKEN BioResource Center, the effect of 2-Cl-C.OXT-A of Example 1 on the differentiation of PC12 cells was examined.

Three samples were prepared by adding additives shown in Table 5 below to PBS so as to achieve predetermined concentrations. Also, an evaluation medium was prepared by adding each sample or PBS to DMEM (no serum) so that its concentration became 10 v/v %. Furthermore, as a control medium, a medium containing only DMEM (no serum) was prepared. The PC12 cells were suspended at a density of $5 \times 10^4$ cells/ml in DMEM to which 5 v/v % cow serum and 10 v/v % horse serum had been added. Thus, a cell suspension was prepared. 3 ml of the cell suspension was inoculated into a 6 petri dish. The replacement with the evaluation medium was conducted on the second day of the culture, and the cells were cultured for another 4 days. On the sixth day of the culture, the cells were photographed under a microscope, and the AChE activity was measured according to the Ellman's method (Ellman, G. L., et al., Biochem. Pharmacol., 7, pp. 88-95, (1961)). Specifically, the AChE activity was measured in the following manner. After the culture, the PC12 cells were scraped with a cell scraper and collected. The collected cells were centrifuged lightly (1200 rpm, 15 minutes), and the supernatant was removed. Then, 150 μl of a 0.1 w/v % Triton (registered trademark) X-100 aqueous solution was added, thus preparing a sample solution. The sample solution, 75 μl of 10 mmol/l DTNB, and 3.0 ml of 0.1 mol/l phosphate buffer solution (pH 8.0) were added to a 75 μl cuvette for absorbance measurement, and finally, 50 μl of 100 mmol/l acetylthiocholine was added to cause a reaction. The absorbance of the reaction solution at 412 nm was measured for 5 minutes from immediately after the addition of the acetylthiocholine. From the thus-measured absorbances, the amount of increase in absorbance (C) per minute was determined. Furthermore, using a PIERCE (registered trademark) BCA Protein Assay Kit (Thermo Fisher Scientific), the protein concentration (D) in the sample solution was measured. The AChE activity was calculated by substituting the amount of increase in absorbance (C) and the protein concentration CD) into the following equation (IV). Note here that 1 U is an amount of enzyme (pmol/min) required to produce 1 μmol of a reaction product per minute. Then, the relative value (-fold) of the AChE activity was calculated by substituting the measured value of AChE into the following equation (V).

$$AChE\ activity(U/mg) = 3.14 \times (C/D) \qquad (IV)$$

$$\text{Relative value (-fold) of } AChE = F/E \qquad (V)$$

E=measured value of AChE in control medium
F=measured value of AChE in each additive-containing medium

TABLE 5

| Sample | Additive | Concentration |
|---|---|---|
| sample 1 | NGF | 1 μg/ml |
| sample 2 | 2-Cl—C•OXT-A | 500 μmol/l |
| sample 3 | 2-Cl—C•OXT-A | 1 mmol/l |

Figure 15A:
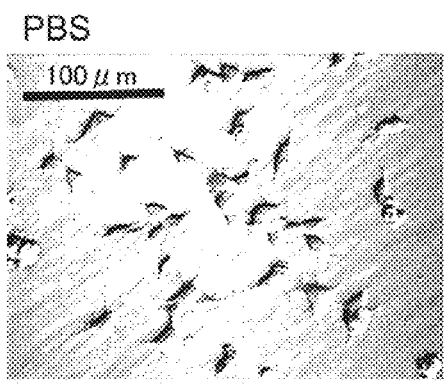
FIG. 15A is a micrograph of the PC12 cells when PBS was used.
Figure 15B:
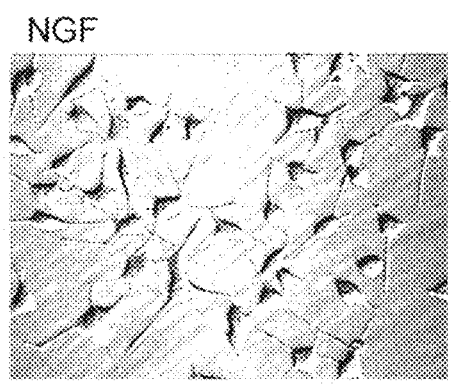
FIG. 15B is a micrograph of the PC12 cells when NGF was used.
Figure 15C:
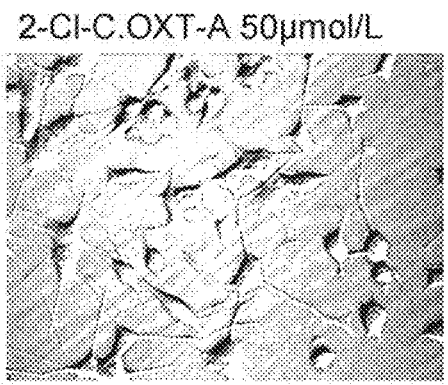
FIG. 15C is a micrograph of the PC12 cells when the medium containing 2-Cl-C.OXT-A at 50 μmol/l was used.
Figure 15D:
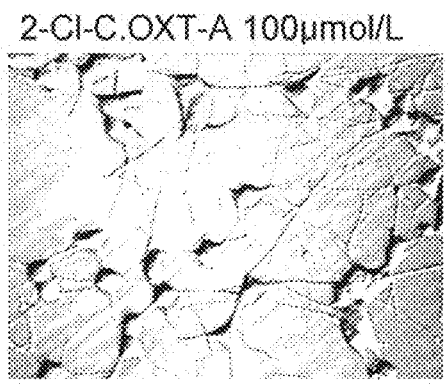
FIG. 15D is a micrograph of the PC12 cells when the medium containing 2-Cl-C.OXT-A at 100 μmol/l was used.

<Morphological Change>
FIGS. 15A to 15D are micrographs of the PC12 cells. FIG. 15A is a micrograph of the PC12 cells cultured in PBS, FIG. 15B is a micrograph of the PC12 cells cultured in the medium containing NGF (nerve growth factor, positive control), FIG. 15C is a micrograph of the PC12 cells cultured in the medium containing 2-Cl-C.OXT-A at 50 μmol/l, and FIG. 15D is a micrograph of the PC12 cells cultured in the medium containing 2-Cl-C.OXT-A at 100 μmol/l. The length of the bar shown in FIG. 15A is 100 μm. In FIG. 15, cells from which linear axons extend are the PC12 cells that had differentiated into neurocyte-like cells. As can be seen from FIG. 15A, in the control, cells from which linear axons extend substantially were not observed. In contrast, as can be seen from FIGS. 15C and 15D, owing to the addition of 2-Cl-C.OXT-A, cells from which linear axons extend were observed as in the case where NGF was added, shown in FIG. 15B.

Figure 16:
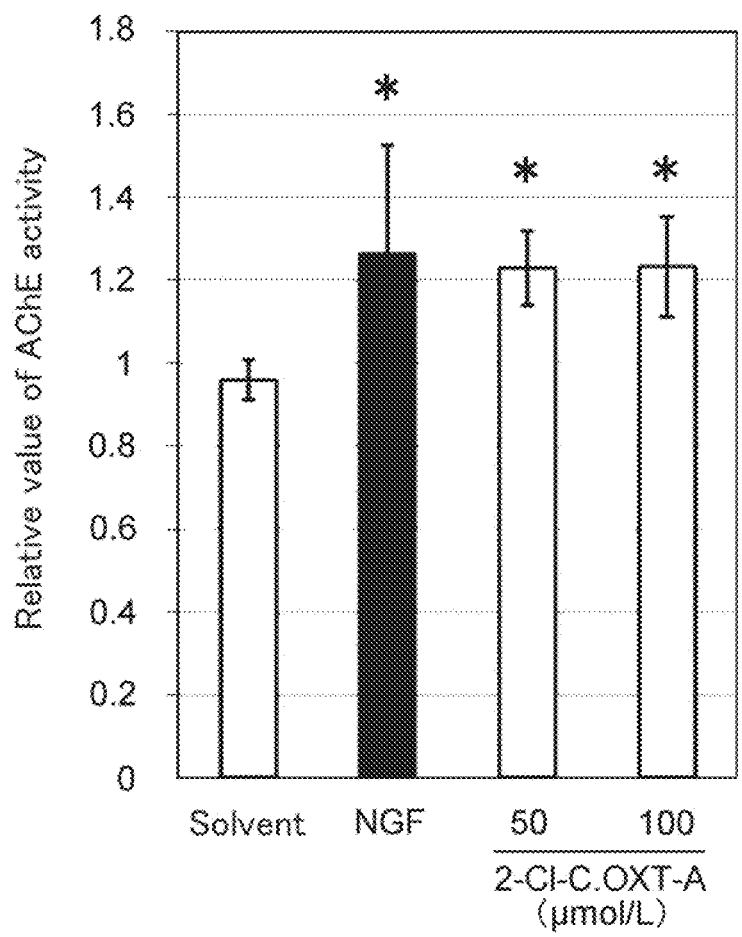
FIG. 16 is a graph showing the results of the AChE activity measurement in Example 10.

<AChE Activity>
FIG. 16 shows the results of measuring the AChE (acetylcholinesterase) activity. The AChE activity is a marker of the differentiation of PC12 cells. In FIG. 16, the vertical axis indicates the relative value of the AChE activity, and the respective bars indicate, from the left, the results obtained when PBS, NGF (positive control), 2-Cl-C.OXT-A (50 μmol/l), and 2-Cl-C.OXT-A (100 μmol/l) were used. As can be seen from FIG. 16, the AChE enzyme activity was increased by 2-Cl-C.OXT-A, as in the case where NGF was added. As is clear from the results, an activity for promoting the differentiation into neurocyte-like cells by 2-Cl-C.OXT-A was exhibited, so that the neurocyte growth promoting-activity of 2-Cl-C.OXT-A was confirmed.

Example 11

In the present example, the effect of 2-Cl-C.OXT-A of Example 1 on angiogenesis was examined by a rabbit cornea assay.

A sample was prepared by adding 2-Cl-C.OXT-A to 30 µl of physiological saline so that its concentration became 16 mmol/l. The sample was injected to a cornea of Japanese white rabbit (male, 2.8 kg) under sevoflurane anesthesia. The cornea was observed after a lapse of 7 days.

Figure 17A:
FIG. 17A is a photograph showing the result obtained after the administration of physiological saline.
Figure 17B:
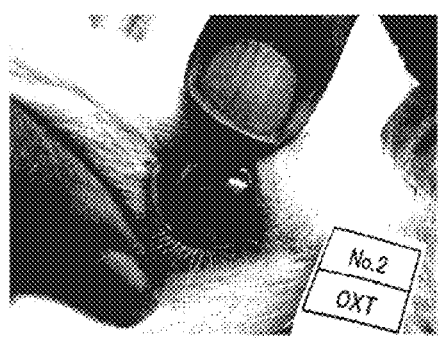
FIG. 17B is a photograph showing the result obtained after the administration of 2-Cl-C.OCT-A.

FIG. 17 shows the results of observation of the eyeball of the rabbit. FIG. 17A is a photographs showing the result obtained when physiological saline was administered, and FIG. 17B is a photographs showing the result obtained when 2-Cl-C.OXT-A was administered. As can be seen from FIG. 17A, after the administration of physiological saline, no angiogenesis was observed. In contrast, as can be seen from FIG. 17B, after the administration of 2-Cl-C.OXT-A, considerable angiogenesis was seen in the cornea. Thus, through the in vivo experiment according to a rabbit cornea assay, the angiogenesis promoting-activity of 2-Cl-C.OXT-A was confirmed.

As is clear from Examples 1 to 11 and Comparatives Example 1 to 10 described above, the cell proliferation promoting-activity, the angiogenesis promoting-activity, the lumen formation promoting-activity, the cell migration promoting-activity, and the neurocyte growth promoting-activity of the cyclobutyl purine derivative according to the present invention were confirmed.

Example 12

The effect of 9-[trans-trans-2,3-bis(acetyloxymethyl)cyclobutyl]guanine represented by the following chemical formula (17) on the cell proliferation, lumen formation, and cell migration of vascular endothelial cells was examined in the same manner as in Example 1. As a result, the compound represented by the following chemical formula (17) exhibited cell proliferation promoting-activity, lumen formation promoting-activity, and cell migration promoting-activity for vascular endothelial cells.

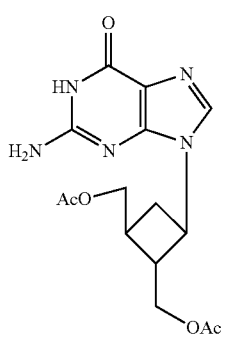

(17)

9-[trans-trans-2,3-bis(acetyloxymethyl)cyclobutyl]guanine represented by the chemical formula (17) can be synthesized as appropriate by a known method. Specifically, it can be obtained by acetylating C.OXT-G (2-amino-9-[trans-trans-2,3-bis(hydroxymethyl)cyclobutyl]-3H-purine-6-one, i.e., 9-[trans-trans-2,3-bis(hydxoxymethyl)cyclobutyl]guanine) represented by the above chemical formula (12) with acetic anhydride in an acetonitrile solvent in the presence of triethylamine and 4-dimethylaminopyridine. This synthesis method is described in JP 03 (1991)-047169 A, U.S. Pat. No. 5,153,352 A, and EP 0366059 A2, for example. Also, C.OXT-G (2-amino-9[trans-trans-2,3-bis(hydroxymethyl)cyclobutyl]-3H-purine-6-one, i.e., 9-[trans-trans-2,3-bis (hydroxymethyl)cyclobutyl]guanine) represented by the above chemical formula (12) can be synthesized as appropriate by a known method, and the synthesis method is described in JP 03 (1991)-047169 A, U.S. Pat. No. 5,153,352 A, and EP 0366059 A2, for example.

Example 13

In the present example, 8-bromo-9-[trans-trans-2,3-bis(acetyloxymethyl)cyclobutyl]guanine represented by the following chemical formula (18) was synthesized.

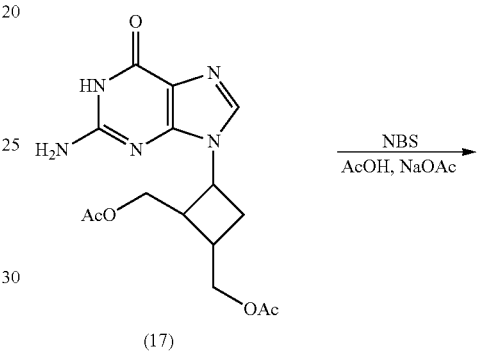

(17)

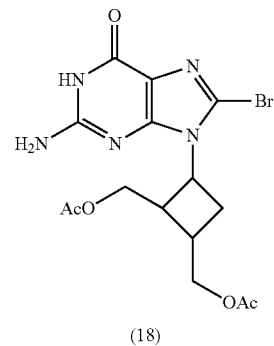

(18)

First, 175 mg (0.5 mmol) of 9-[trans-trans-2,3-bis(acetyloxymethyl)cyclobutyl]guanine represented by the chemical formula (17) was dissolved in 3.5 ml of acetic acid, and 175 mg of sodium acetate was added further thereto and dissolved therein. This solution is referred to as an "A solution". On the other hand, 110 mg (0.62 mmol) of N-bromosuccinimide was dissolved in 2 ml of acetic acid. This solution is referred to as a "B solution". The B solution was dripped into the A solution while stirring. This mixed solution was allowed to stand at room temperature for 30 minutes, and further was allowed to stand at 4° C. overnight. Thereafter, the solvent was evaporated under reduced pressure, and the residual substance obtained was dissolved in a mixture of 20 ml of ethyl acetate and 10 ml of water. The aqueous layer was separated from this mixture, and the organic layer was concentrated, which caused crystals to precipitate. Furthermore, crystals precipitated also from the separated aqueous layer. The crystals having precipitated from the organic layer and the aqueous layer respectively were collected by filtering and then dried. Thus, the desired compound, 8-bromo-9-[trans-trans-2,3-bis acetyloxymethyl)cyclobutyl]guanine (18), was obtained with a yield of 154 mg (0.40 mmol, yield 80%). Physical properties of this compound are shown below.

FT-MS m/z=450, 452 (M$^+$+Na); $^1$H NMR (400 MHz, DMSO-d$_6$): δ10.76 (1H, br s), 6.48 (2H, br s), 4.58 (1H, m), 4.21 (3H, d, J=7.2 Hz), 4.07 (3H, d, J=6.0 Hz), 3.42 (1H, m), 2.81 (1H, m), 2.35 (1H, m), 2.22 (1H, m), 2.02 (3H, s), 1.92 (3H, s)

The effect of this 8-bromo-9-[trans-trans-2,3-bis(acetyloxymethyl)cyclobutyl]guanine (chemical formula (18)) on the cell proliferation, lumen formation, and cell migration of vascular endothelial cells was examined in the same manner as in Example 1. As a result, this compound exhibited cell proliferation promoting-activity, lumen formation promoting-activity, and cell migration promoting-activity for vascular endothelial cells.

Example 14

8-bromo-9-[trans-trans-2,3-bis(hydroxymethyl)cyclobutyl]guanine represented by the following chemical formula (19) was synthesized.

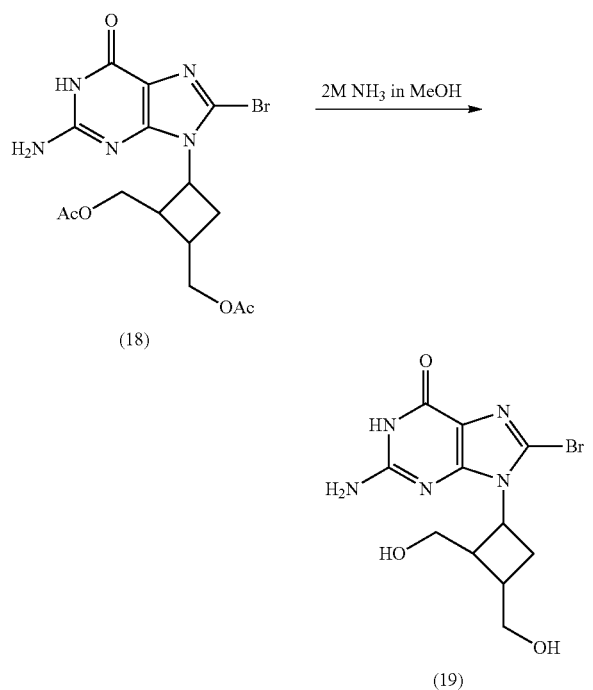

39 mg (0.091 mmol) of 8-bromo-9-[trans-trans-2,3-bis (acetyloxymethyl)cyclobutyl]guanine represented by the chemical formula (18) was dissolved in 5 ml of 2M ammonia methanol solution, and the resultant solution was allowed to stand at 25° C. for 1 day. By concentrating this solution, the desired compound, 8-bromo-9-[trans-trans-2,3-bis(hydroxymethyl)cyclobutyl]guanine (19), was obtained in the form of slightly yellowish crystals. The yield was 21 mg (0.061 mmol, yield: 67%). Physical properties of this compound are shown below.

FT-MS m/z=366, 368 (M$^+$+Na); $^1$H NMR (400 MHz, DMSO-d$_6$): δ8.52 (1H, br s), 6.47 (2H, br s), 4.60 (2H, m), 4.50 (1H, t, J=5.2 Hz), 3.59 (2H, t, J=5.6 Hz), 3.43 (2H, t, J=4.8 Hz), 3.25 (1H, m), 2.57 (1H, q, J=10.0 Hz), 2.26 (1H, m), 2.02 (1H, m).

The effect of this 8-bromo-9-[trans-trans-2,3-bis(hydroxymethyl)cyclobutyl]guanine (chemical formula (19)) on the cell proliferation, lumen formation, and cell migration of vascular endothelial cells was examined in the same manner as in Example 1. As a result, this compound exhibited cell proliferation promoting-activity, lumen formation promoting-activity, and cell migration promoting-activity for vascular endothelial cells.

Example 15

2-amino-6,8-dichloro-9-[trans-trans-2,3-bis(acetyloxymethyl)cyclobutyl]purine represented by the following chemical formula (20) was synthesized.

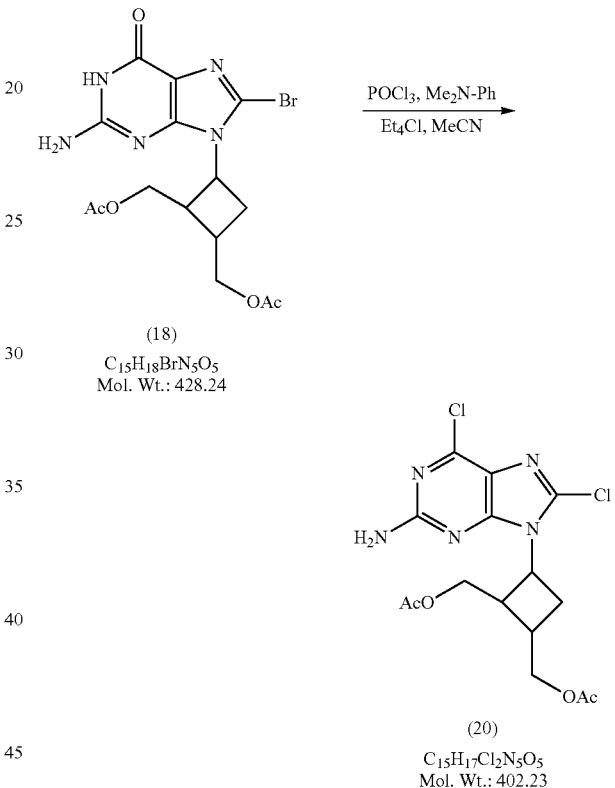

First, 154 mg (0.4 mmol) of 8-bromo-9-[trans-trans-2,3-bis (acetyloxymethyl)cyclobutyl]guanine represented by the chemical formula (18) and 150 mg of tetraethylammonium chloride were dissolved in 5 ml of acetonitrile. 0.16 ml (1.3 mmol) of N,N-dimethylaniline and 0.7 ml (7.7 mmol) of phosphorus oxychloride were added further to this solution, and the resultant solution was allowed to stand at room temperature for 30 minutes. It was then heat-refluxed at 100° C. for 30 minutes to cause a reaction. Thereafter, the reaction solution was dripped into ice water, and stirred for 15 minutes. Then, the desired compound was extracted with chloroform. The chloroform layer was washed with 5% sodium hydrogencarbonate water and water, was concentrated, and then separated by silica gel column chromatography (hexane: ethyl acetate=2:1). Thus, the desired compound, 2-amino-6, 8-dichloro-9-[trans-trans-2,3-bis(acetyloxymethyl)cyclobutyl]purine (20), was obtained in the form of white crystals. The yield was 86 mg (0.21 mmol, yield 53%). Physical properties of this compound are shown below.

FT-MS m/z=424, 426, 428 (M⁺+Na): ¹H NMR (400 MHz, CDCl₃): δ5.16 (2H, br s), 4.70 (1H, m), 4.35 (2H, d, J=6.4 Hz), 4.17 (2H, m), 3.62 (1H, m), 2.89 (1H, m), 2.52 (1H, m), 2.33 (1H, m), 2.10 (3H, s), 2.02 (3H, s).

The effect of this 2-amino-6,8-dichloro-9-[trans-trans-2,3-bis(acetyloxymethyl)cyclobutyl]purine (chemical formula (20)) on the cell proliferation, lumen formation, and cell migration of vascular endothelial cells was examined in the same manner as in Example 1. As a result, this compound exhibited cell proliferation promoting-activity, lumen formation promoting-activity, and cell migration promoting-activity for vascular endothelial cells.

Example 16

2-amino-6,8-dimethoxy-9-[trans-trans-2,3-bis(hydroxymethyl)cyclobutyl]purine represented by the following chemical formula (21) was synthesized.

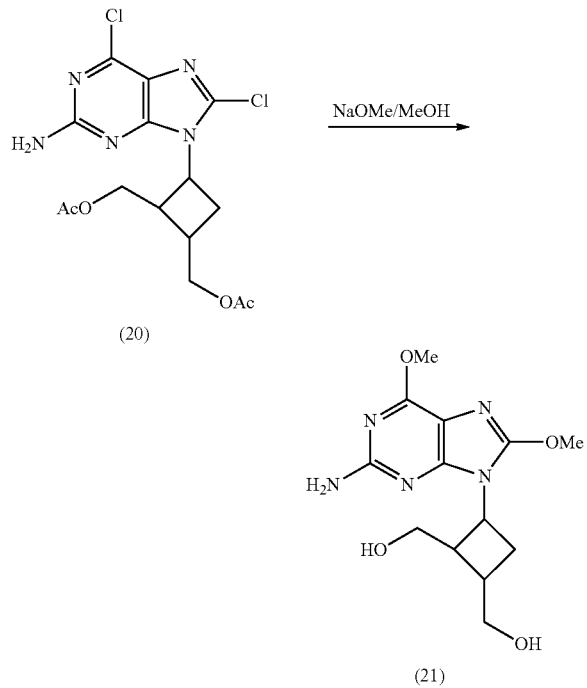

First, 75 mg (0.186 mmol) of 2-amino-6,8-dichloro-9-[trans-trans-2,3-bis(acetyloxymethyl)cyclobutyl]purine represented by the chemical formula (20) was suspended in 6 ml of methanol. 0.5 ml of 23% sodium methoxide was added further to this suspension and stirred, whereby the raw material compound (20) was dissolved in the methanol. This solution was heated at 60° C. overnight to cause a reaction. After the reaction, the solution was neutralized with acetic acid and then was concentrated. Thereafter, it was separated by silica gel column chromatography (ethyl acetate:methanol=12:1), and the solvent was evaporated. The residual substance obtained was crystallized (recrystallized) from ethyl acetate. As a result, the desired compound, 2-amino-6,8-dimethoxy-9-[trans-trans-2,3-bis(hydroxymethyl)cyclobutyl]purine (21), was obtained in the form of white crystals. The yield was 34.4 mg (0.111 mmol, yield 60%). Physical properties of this compound (21) are shown below.

FT-MS m/z=310 (M⁺+H): ¹H NMR (400 MHz, DMSO-d₆): δ 4.44-55 (3H, m), 3.99 (3H, s), 3.88 (3H, s), 3.52 (2H, t, J=6.0 Hz), 3.40 (2H, t, J=5.2 Hz), 3.01 (1H, m), 2.31 (1H, m), 2.20 (1H, m), 1.98 (1H, m).

The effect of this 2-amino-6,8-dimethoxy-9-[trans-trans-2,3-bis(hydroxymethyl)cyclobutyl]purine (chemical formula (21)) on the cell proliferation, lumen formation, and cell migration of vascular endothelial cells was examined in the same manner as in Example 1. As a result, this compound exhibited cell proliferation promoting-activity, lumen formation promoting-activity, and cell migration promoting-activity for vascular endothelial cells.

INDUSTRIAL APPLICABILITY

The cyclobutyl purine derivative, the tautomer or stereoisomer thereof, or the salt, solvate, or hydrate thereof according to the present invention is a chemically stable low molecular weight substance and has high absorbability because of its low molecular weight. Furthermore, the cyclobutyl purine derivative, the tautomer or stereoisomer thereof, or the salt, solvate, or hydrate thereof according to the present invention can be produced industrially, so that it can be supplied stably at a low cost. The cyclobutyl purine derivative, the tautomer or stereoisomer thereof, or the salt, solvate, or hydrate thereof according to the present invention can be used in various kinds of drugs, quasi drugs, and the like that utilize at least one of cell proliferation promoting-activity, angiogenesis promoting-activity, lumen formation promoting-activity, cell migration promoting-activity, and neurocyte growth promoting-activity. It is applicable to a broad range of fields without limitation.

The invention claimed is:

1. A cyclobutyl purine derivative represented by the following formula (1), a tautomer or a stereoisomer thereof, or a salt thereof:

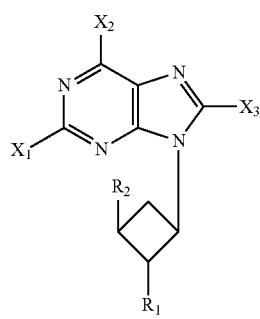

where:
X₁ is chlorine;
X₂ is NH₂;
X₃ is a hydrogen atom; and
each of R₁ and R₂ is C₂OH.

2. The cyclobutyl purine derivative according to claim 1, the tautomer or the stereoisomer thereof, or the salt thereof, which is 6-amino-2-chloro-9-[trans-trans-2,3-bis(hydroxymethyl)cyclobutyl]purine a tautomer or a stereoisomer thereof, or a salt, a solvate, or a hydrate thereof.

3. A promoting agent having at least one function selected from the group consisting of an angiogenesis-promoting function, a lumen formation-promoting function, and a neurocyte growth-promoting function, the promoting agent comprising:
a cyclobutyl purine derivative that is represented by following formula (1'), a tautomer or a stereoisomer thereof, or a salt thereof:

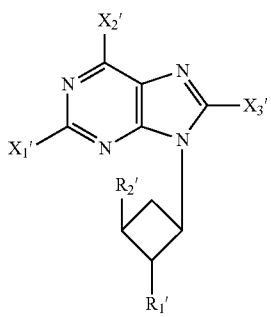

where:
$X_1'$ is chlorine;
$X_2'$ is $NH_2$;
$X_3'$ is a hydrogen atom; and
each of $R_1'$ and $R_2'$ is $CH_2OH$.

4. A promoting agent having at least one function selected from the group consisting of an angiogenesis-promoting function, a lumen formation-promoting function, and a neurocyte growth-promoting function, the promoting agent comprising:

the cyclobutyl purine derivative according to claim 2, the tautomer or the stereoisomer thereof, or the salt thereof.

5. A drug having at least one function selected from the group consisting of promoting angiogenesis, promoting lumen formation, and promoting neurocyte growth, the drug comprising:

at least one compound selected from the group consisting of the cyclobutyl purine derivative according to claim 3, the tautomers and the stereoisomers thereof, the salts thereof and at least, one pharmaceutically acceptable additive.

* * * * *